United States Patent
Udpa et al.

(10) Patent No.: US 7,425,193 B2
(45) Date of Patent: Sep. 16, 2008

(54) TOMOGRAPHIC IMAGING SYSTEM USING A CONFORMABLE MIRROR

(75) Inventors: Satish S. Udpa, Okemos, MI (US); Lalita Udpa, Okemos, MI (US)

(73) Assignee: Michigan State University, East Lansing, MI (US)

( * ) Notice: Subject to any disclaimer, the term of this patent is extended or adjusted under 35 U.S.C. 154(b) by 0 days.

(21) Appl. No.: 11/438,639

(22) Filed: May 22, 2006

(65) Prior Publication Data

US 2006/0239404 A1    Oct. 26, 2006

Related U.S. Application Data

(63) Continuation-in-part of application No. 11/407,665, filed on Apr. 20, 2006, now Pat. No. 7,336,761.

(60) Provisional application No. 60/683,639, filed on May 23, 2005, provisional application No. 60/673,605, filed on Apr. 21, 2005.

(51) Int. Cl.
   *A61H 1/00*    (2006.01)
(52) U.S. Cl. .................................. 600/2; 601/2; 604/22

(58) Field of Classification Search ............. 378/64–65; 600/14, 2, 439; 601/2; 604/22
See application file for complete search history.

(56) References Cited

U.S. PATENT DOCUMENTS

| 6,108,121 A | 8/2000 | Mansell et al. |
| 6,366,801 B1 * | 4/2002 | Cash et al. .................. 600/431 |
| 6,580,940 B2 * | 6/2003 | Gutman ...................... 600/427 |
| 2002/0080916 A1 * | 6/2002 | Jiang et al. .................... 378/84 |

* cited by examiner

*Primary Examiner*—Hoon Song
(74) *Attorney, Agent, or Firm*—Price, Heneveld, Cooper, DeWitt & Litton, LLP

(57) ABSTRACT

A tomographic imaging system comprising a source array emitting rays, a deformable mirror reflecting the rays emitted by the source array, and a detector array receiving the electromagnetic rays emitted by the source array and reflected by the deformable mirror. An object can be positioned between the deformable mirror and the detector array and the deformable mirror can be deformed to a plurality of configurations to form a tomographic image of the object. The system can also be used in radiation therapy.

2 Claims, 20 Drawing Sheets
(15 of 20 Drawing Sheet(s) Filed in Color)

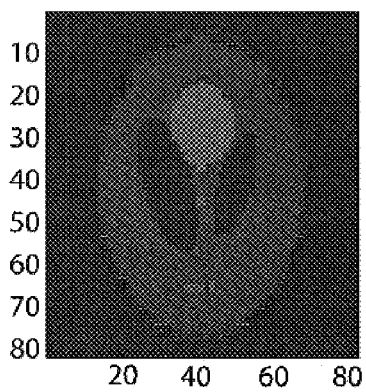 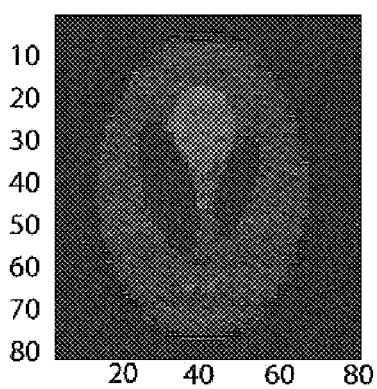 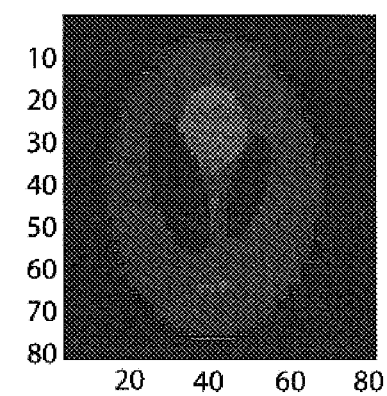
FIG. 7A          FIG. 7B          FIG. 7C
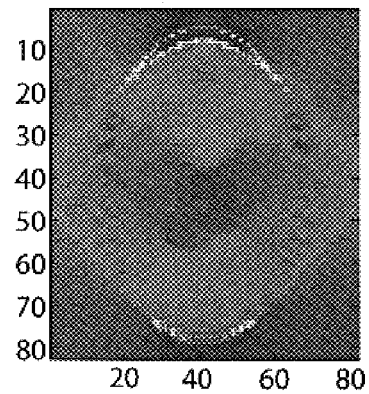 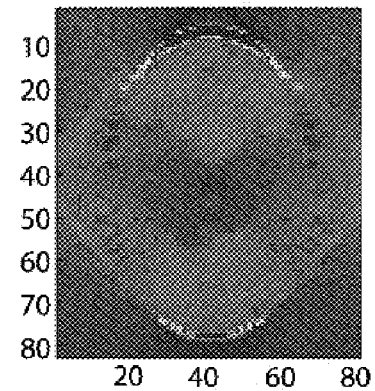 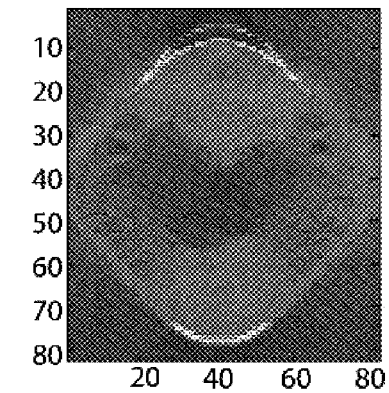
FIG. 7D          FIG. 7E          FIG. 7F

TOMOGRAPHIC IMAGING SYSTEM USING A CONFORMABLE MIRROR

CROSS-REFERENCE TO RELATED APPLICATIONS

This application is a continuation-in-part of U.S. patent application Ser. No. 11/407,665 filed on Apr. 20, 2006, now U.S. Pat. No. 7,336,761, which claims priority to U.S. Provisional Application No. 60/673,605, filed on Apr. 21, 2005 and U.S. Provisional Application No. 60/683,639 filed on May 23, 2005. The present application also claims priority to U.S. Provisional Application No. 60/683,639 filed on May 23, 2005.

FIELD OF THE INVENTION

The present invention concerns a tomographic imaging system, and more particularly relates to a tomographic imaging system using a conformable mirror.

BACKGROUND OF THE INVENTION

Computed tomography (CT) is a mature imaging technique that involves reconstruction of 2D cross sectional images of a 3D object using projection data. CT has a wide range of applications in medical imaging as a diagnostic tool, of which the first important example is X-ray tomography.

X-ray CT has a wide range of applications as a diagnostic tool in such disciplines as medicine, geology, anthropology and engineering science for visualizing the interior structure of solid objects. Of all the diagnostic tools, namely transmission tomography (X-ray), emission tomography (radioactive isotopes), ultrasound and magnetic resonance, X-ray CT was the first tool that revolutionized diagnostic medicine. Even though the mathematical foundation of image reconstruction from tomographic projection was first laid in 1917, avid interest in tomographic reconstruction began only after the invention of the X-ray tomography scanner in 1972. Since then several advances have been made resulting in fast and efficient data collection and reconstruction algorithms.

Over the past three decades, CT has evolved into a key diagnostic tool with a myriad of applications. Based on scanning configuration, motion, beam geometry and detector arrangements; several generations of CT scanners have evolved. Current CT scanners are often referred to as 3rd, 4th or 5th generation systems. The CT scanners to date have used parallel, fan or cone beam sources with translate/rotate, rotate/rotate, rotate-stationary and stationary-stationary (source and detectors are fixed on a circular array) scan configurations for projection measurements. All these scan geometries require precise positioning and alignment of the source-detector pairs. In some applications, the geometry of the object under diagnosis limits the scanning angle to less than 180 or 360 degrees, thereby affecting the quality of the reconstructed two dimensional cross sections. Besides these experimental and algorithmic limitations, the closed chamber of the CT scan equipment induces discomfort in claustrophobic patients and children.

Additionally, the increased level of terrorist activities has elevated the need for efficient screening of cargo containers and vehicles at ports of entry for the detection of contraband goods, collection of duties and minimizing illegal activities. It is desirable for any viable screening technique to be nondestructive, be non-intrusive (i.e., allowing inspection of sealed containers), yield high resolution images, and possess high sensitivity for contraband goods. X-ray CT has a wide range of applications as a diagnostic tool for visualizing the interior structure of solid objects. High energy X-rays (2-12 MeV) can penetrate large, high density objects and objects with a high atomic number. Such materials are often used for packaging contraband freight. At high energy, X-rays can penetrate steel walls that are ~400 mm thick and offer excellent resolution ~5 mm. Although high energy CT is a promising imaging modality for border security applications, its use has been prevented by the difficulty associated with rotating the detector/source pair around the test object. Consequently, most cargo inspection systems rely on simple systems that can provide only 2D projection images. Such images are difficult to interpret and it is often possible to hide contraband goods behind other benign looking objects. A missed detection due to poor resolution in the reconstructed image may lead to a breach of national security or contribute to illegal trafficking of drugs and weapons.

Accordingly, an apparatus is desired having the aforementioned advantages and solving and/or making improvements on the aforementioned disadvantages.

SUMMARY OF THE PRESENT INVENTION

An aspect of the present invention is to provide a tomographic imaging system comprising a source array emitting rays, a deformable mirror reflecting the rays emitted by the source array, and a detector array receiving the rays emitted by the source array and reflected by the deformable mirror. An object can be positioned between the deformable mirror and the detector array and the deformable mirror can be deformed to a plurality of configurations to form a tomographic image of the object.

Another aspect of the present invention is to provide a method of forming a tomographic image of an object comprising emitting rays with a source array emitting rays, reflecting the rays emitted by the source array off of a deformable mirror, and receiving the rays emitted by the source array and reflected by the deformable mirror with a detector array. The method also includes positioning an object between the deformable mirror and the detector array and deforming the deformable mirror to a plurality of configurations to form a tomographic image of the object.

Yet another aspect of the present invention is to provide a method of providing cancer therapy to an object comprising emitting rays with a source array reflecting the rays emitted by the source array off of a deformable mirror and into the object, and destroying cancerous cells in the object with energy from the rays.

These and other aspects, objects, and features of the present invention will be understood and appreciated by those skilled in the art upon studying the following specification, claims, and appended drawings.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIGS. 7A-F show LFOV reconstruction results of conventional CT methods, with FIG. 7A illustrating an 81×81 modified Shepp-Logan head phantom image, FIG. 7B illustrating a Kaczmarz reconstruction of the object at a 60th iteration, FIG. 7C illustrating Kaczmarz reconstruction of the object at an 300th iteration, FIG. 7D illustrating a filtered back projection reconstruction with Ram-Lak filter and spline interpolation of the object, FIG. 7E illustrating a filtered back projection reconstruction with Ram-Lak filter and spline interpolation of the object at a 60th iteration, and FIG. 7F illustrating a filtered back projection reconstruction with Ram-Lak filter and spline interpolation of the object an 300th iteration.

DETAILED DESCRIPTION OF PREFERRED EMBODIMENTS

Figure 1:
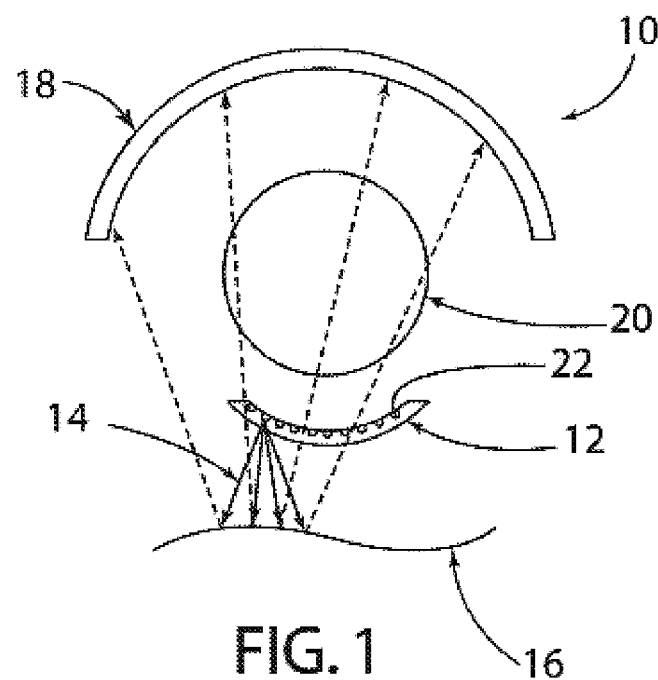
FIG. 1 is a schematic representation of a first embodiment of a tomographic imaging system of the present invention.

For purposes of description herein, the terms "upper," "lower," "right," "left," "rear," "front," "vertical," "horizontal," and derivatives thereof shall relate to the invention as orientated in FIG. 1. However, it is to be understood that the invention may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The reference number 10 (FIG. 1) generally designates a tomographic imaging system embodying the present invention. In the illustrated example, the tomographic imaging system 10 comprises a source array 12 emitting electromagnetic rays 14, a deformable mirror 16 reflecting the electromagnetic rays 14 emitted by the source array 12, and a detector array 18 receiving the electromagnetic rays 14 emitted by the source array 12 and reflected by the deformable mirror 16. An object 20 can be positioned between the deformable mirror 16 and the detector array 18 and the deformable mirror 16 can be deformed to a plurality of configurations to form a tomographic image of the object 20.

The tomographic imaging system 10 of the present invention is preferably used for computed tomography (CT), which is an imaging technique that involves reconstruction of two-dimensional cross-sectional images of a three dimensional object using projection data. However, unlike previous computed tomography systems, the tomographic imaging system 10 of the present invention does not require movement of the source array 12 and/or the detector array 18.

In the illustrated example, the tomographic imaging system 10 of the present invention includes the source array 12. The source array 12 emits electromagnetic rays 14 that reflect off of the deformable mirror 16, through the object 20 and to the detector array 18. It is contemplated that the source array 12 can emit electromagnetic rays 14 including X-ray, microwave, terahertz, optical and other wavelengths, depending on the use of the tomographic imaging system 10. The imaging system 10 could also employ other forms of energy that propagate as waves, such as sound. Although the terms "electromagnetic" and/or "ray" are used, the system 10 could also include these other forms of energy unless expressly stated otherwise. The source array 12 can include a plurality of ray emitters 22 emitting the electromagnetic rays. The ray emitters 22 can be aligned in a line (see, for example, FIG. 2, wherein the ray emitters are designated by the number "22a"), can be aligned in an arc (see, for example, FIG. 1) or can be in any formation. Similarly, the configuration could employ appropriately located multiple deformable mirrors associated with multiple sources. In the illustrated embodiment, the source array 12 is preferably located between the object 20 and the deformable mirror 16. However, it is contemplated that the source array 12 could be located between the object 20 and the detector array 18 or in any other position, depending on the configuration of the tomographic imaging system 10. In the illustrated embodiment, the source array 12 includes the plurality of ray emitters 22 in a fixed position. In use, the ray emitters 22 could be employed one at a time or a plurality of ray emitters 22 could be used simultaneously. In an alternative embodiment, it is contemplated that the source array 12 could include one ray emitter 22 that moves. The source array 12 with one ray emitter would move the ray emitter to sequentially emit rays towards the deformable mirror 16. Preferably, the one ray emitter would sequentially move to a position identical to each position of the plurality of ray emitters 22 of the source array 12 with the plurality of ray emitters 22 (as, for example, those shown in FIG. 1 or FIG. 2). When the source array 12 includes one ray emitter, the movement of the one ray emitter would comprise the source array 12. However, it is contemplated that the source array 12 could include only one stationary ray emitter. Furthermore, the source array 12 could emit the electromagnetic rays 14 in a fixed line, a fan or a cone. In any of the configurations described directly above, the source array 12 directs the electromagnetic rays 14 towards the deformable mirror 16.

Figure 3:
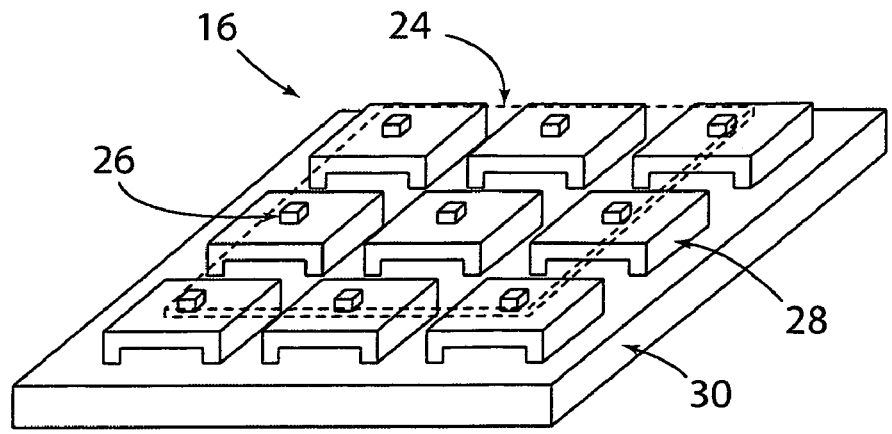
FIG. 3 is a schematic illustration of a deformable mirror of the system of the present invention.

The illustrated deformable mirror 16 can comprise a variety of mechanisms that have been proposed for building mirrors whose shapes can be varied continuously. Preferably, the deformable mirror 16 is a continuously flexible and mechanically stable micro-machined membrane mirror or micro-machined deformable mirror (MMDM). A MMDM is a micro-electro-mechanical system (MEMS) that consists of a flexible membrane controlled by underlying complementary metal-oxide semiconductor (CMOS) circuits. FIG. 3 shows the schematic diagram of a continuous-membrane MMDM device or deformable mirror 16. The deformable mirror 16 comprises a flexible membrane 24 supported by an array of actuator posts 26, with the flexible membrane 24 acting as an elastic thin film (reflective surface) of the deformable mirror 16. An electrostatic actuator structure 28 with attachment posts 26 located at discrete points is connected to a ground substrate 30 and enables a smooth deformation of the flexible membrane governed by the basic vibration theory. When a potential distribution V(x,y) is applied between the actuator structure 28 and the ground substrate 30, an electrostatic force is developed normal to the flexible membrane 24. The electrostatic force deflects the flexible membrane 24 mounted on the actuator post 26, creating a local deformation of the flexible membrane 24, sparing the rest of the flexible membrane 24. The deformable mirror 16 of the illustrated invention is preferably an MMDM device with a suitable X-ray reflective coating. Examples of deformable mirrors 16 are disclosed by G. Vdovin and P. M. Sarro in "Flexible mirror micromachined in silicon," Appl. Opt., 34, pp. 2968-2972, 1995, by T. G. Bifano, R. Krishnamoorthy, J. K. Dorton, J. Perreault, N. Vandelli, M. N. Horenstein, and D. A. Castanon in "Continuous membrane surface-micromachined silicon deformable mirror," Opt. Eng., 36, 1354-1360, May 1997, and in U.S. Pat. No. 6,108,121 entitled Micromachined high reflectance deformable mirror, the entire contents of each of these are incorporated herein by reference. The deformable mirror 16 reflects the electromagnetic rays 14 through the object 20 and to the detector array 18.

In the illustrated example, the detector array 18 receives the electromagnetic rays 14 to determine a tomographic image of the object 20 as discussed in more detail below. The detector array 18 is configured to receive the wavelength of the electromagnetic rays 14 emitted by the source array 12. In the illustrated embodiment, the detector array 18 is preferably located on a side of the object 20 opposite to the source array 12 and deformable mirror 16. However, it is contemplated that the detector array 18 could be located on the same side of the object 20 as the source array 12 or in any other position, depending on the configuration of the tomographic imaging system 10. The detector array 18 can be aligned in a line (see, for example, FIG. 2, wherein the detector array is designated by the number "18a"), can be aligned in an arc (see, for example, FIG. 1) or can be in any formation.

Figure 4:
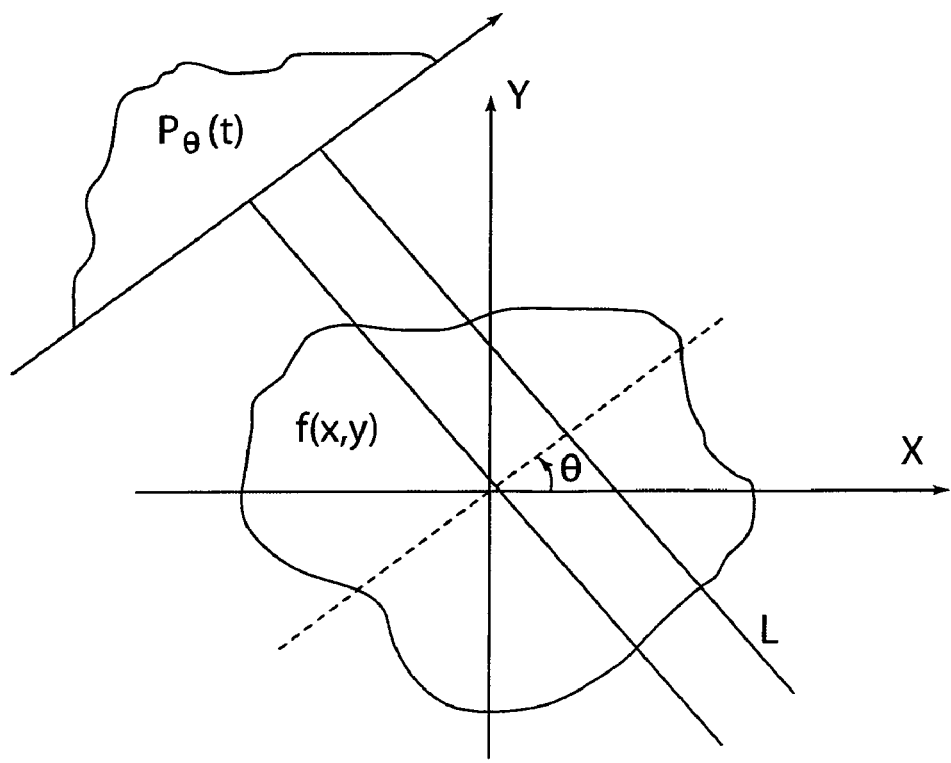
FIG. 4 shows a simplest parallel beam projection of a two-dimensional image at an angle θ from a collimated source emitting a pencil beam.

The objective of the tomographic imaging system of the present invention is to reconstruct a two-dimensional cross section of a three-dimensional object 20 from the ray-sums of projections measured from several source-detector orientations around the object 20. FIG. 4 shows the simplest parallel beam projection of a two-dimensional image at an angle θ from a collimated source emitting a pencil beam. In X-ray CT, projection along a direction θ in the image plane is a set of line integrals of the linear attenuation function f(x,y) of the object given by:

$$g_\theta(t) = \int_{-\infty}^{\infty}\int_{-\infty}^{\infty} f(x,y)\delta(x\cos\theta + y\sin\theta - t)\,dx\,dy \quad (1)$$

The problem of recovery of f(x,y) from $g_\theta(t)$ is a linear inverse problem called as "image reconstruction from projections" or "inverse Radon transform." In discrete form, the projection operation in (1) is modeled as a linear system of the form, $$Af = g \quad (2)$$

Tomographic image reconstruction involves the estimation of the unknown attenuation vector $f^{(0)}$ from the known projections g and mapping function A. For solving (2), many iterative algorithms based on projection methods are available, of which the algorithm proposed by Kaczmarz are preferably used. Other approaches for reconstruction can also be used. For a nxn linear attenuation function represented in an N dimensional image space $(f_1, f_2, \ldots, f_N)$ with $N=n^2$, the projection of the $i^{th}$ ray $g_i$ in (2) is related to the $f_j$s by $$\sum_{j=1}^{N} a_{ij} f_j = g_i, i = 1, 2, \ldots, N \quad (3)$$

where $a_{ij}$'s denote the contribution of the $j^{th}$ image cell to the $i^{th}$ ray sum. The Kaczmarz algorithm starts with an initial estimate $f^{est}$ and projects the estimate on the hyperplanes in (3) until convergence is obtained. In mathematical form, the $k^{th}$ successive projection is expressed as $$f^k = f^{k-1} + \frac{(g_i - a_i^T f^{k-1})}{a_i^T a_i} a_i, i = 1, 2, \ldots, M \quad (4)$$

where $f^k$ is the $k^{th}$ estimate of $f^{(0)}$ and $a_i^T$ is the $i^{th}$ row vector $(a_{i1}, a_{i2}, \ldots, a_{iN})$ in A. If a unique solution exists, a successive projection of the estimate (4) onto the hyperplanes (3) will converge to the true solution in the limit.

FIG. 1 illustrates a schematic diagram of a first embodiment of the tomographic imaging system 10 of the present invention for a MMDM based X-ray CT technique for biomedical imaging. The illustrated system comprises a fan beam source array 12 and the detector array 18 both on an annular ring about the object's (e.g., a patient's) isocenter in a transverse imaging plane. The deformable mirror 16 is a continuous-membrane deformable X-ray reflecting mirror placed in the imaging plane on the same side as the source array 12. The configuration of the system 10 has limited field-of-view (LFOV) as the X-ray source array 12 is moved to few predetermined locations during projection measurement. In this quasi-stationary scan arrangement, the detector array 18 and the flexible deformable mirror 16 remain stationary.

During data collection, for each fan beam source position (i.e., position of the ray emitters 22 of the source array 12), projection data is collected for different unique mirror deflections W(x,y) by applying an appropriate potential distribution V(x,y) on the source array 12. Depending on the mirror deflection W(x,y), the incident X-ray gets diverted along a path governed by Bragg's law of reflection and is measured at the detector array 18 after traversing via the object 20 under examination. From the knowledge of the X-ray reflective coating on the MEMS mirror 16, the energy of the reflected ray 14 can easily be determined. Using the Bragg angle of the reflective coating and ray tracing technique, the path traversed by each X-ray 14 from the source array 12 to the detector array 18 via the region of interest (i.e., through the object 20) can be determined and the image to projection space mapping function A can be constructed. The projection data collected using unique mirror shapes together with the mapping function A aids in reconstructing the two-dimensional slice of the three-dimensional object 20 using the iterative Kaczmarz algorithm.

The quasi-stationary scan configuration in the system 10 potentially has minimal source-detector alignment errors and the data acquisition speed can be accelerated with the hysteresis-free MEMS X-ray mirror 16. Minimal source movement with stationary detector array 18 in conventional CT systems results in LFOV imaging. A major concern with LFOV imaging in contemporary CT systems is limited angle projection data that leads to poor resolution and partial image reconstruction. Unlike contemporary CT systems, in the system 10 of the present invention, even with LFOV, a voluminous amount of projection data can be collected using a multitude of mirror 16 shapes. For unique and information-rich projection data, an optimal set of mirror deflections can be predetermined based on the geometry of the object 20 being imaged.

Figure 1A:
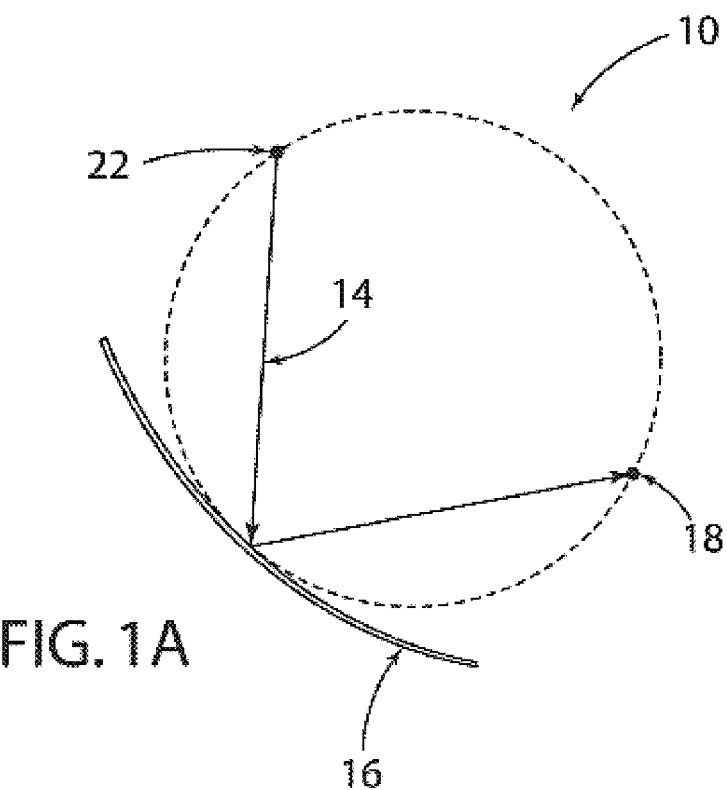
FIG. 1A is a schematic diagram of the system setup positioned in Rowland circle geometry for radiation therapy.

The system 10 of FIG. 1 can also be used in MEMS based cancer therapy for destroying cancerous cells. Apart from its use as a CT imaging system, the illustrated system 10 configuration can be used for therapy. In therapy, cancerous cells are destroyed by radiation by delivering a high dose of high-energy photons or by heat generated by the absorption of acoustic or microwave energy from ultrasonic waves or microwaves, respectively. FIG. 1A shows the schematic diagram of the adaptive mirror setup positioned in Rowland circle geometry for cancer therapy. In the Rowland circle geometry, each ray from a point source (emitter 22) impinges on the mirror 16 at the same angle and is focused back to an image point of the point source on the same circle. In FIG. 1, the source array 12, the detector array 18 and the deformable X-ray mirror 16 lie on a circle with a diameter equal to the radius of curvature of the X-ray mirror 16. During therapy, the object 20 is immobilized and remains in the same position as it was during imaging as described above. Using the reconstructed CT image, the positions of the source array 12, the detector array 18 and the mirror 16 are aligned to lie on an appropriate Rowland circle and by applying a suitable potential distribution V(x,y), a mirror deflection W(x,y) with radius of curvature equal to the diameter of the Rowland circle is achieved. With the source array 12 and the mirror 16 aligned at Bragg angle, the incident X-ray 14 gets effectively focused at the tumor site with minimal collateral damage to adjacent healthy tissue.

Figure 1B:
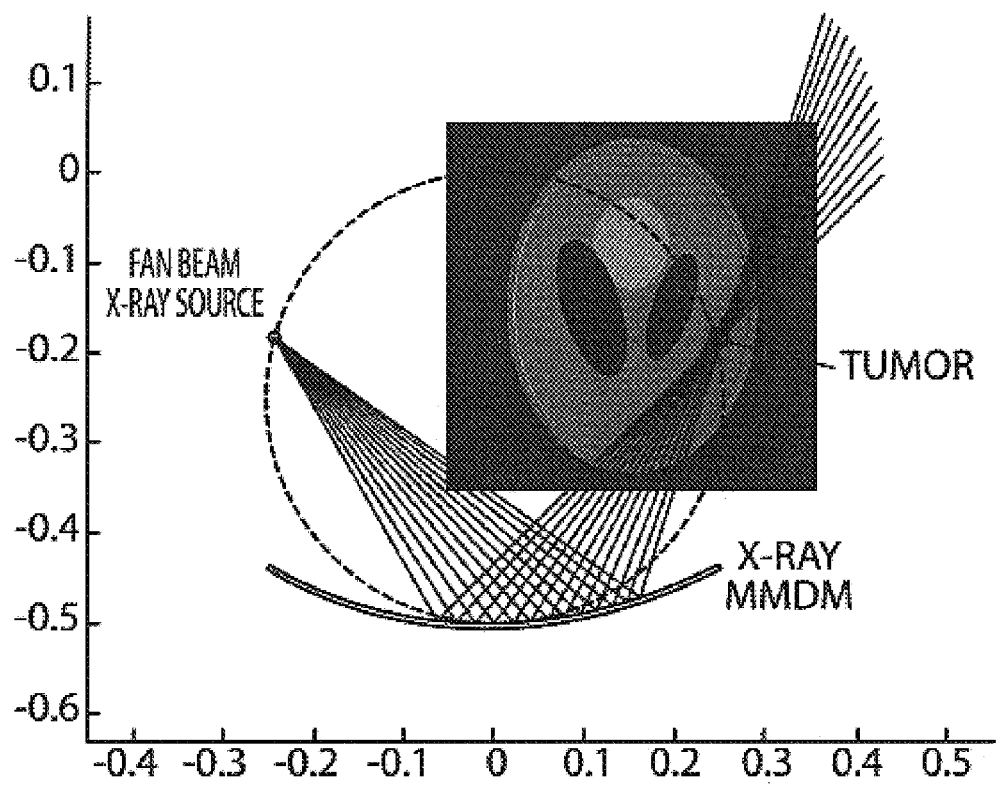
FIG. 1B illustrates use of the system for therapy.

The X-ray reflective MMDM device in the Rowland circle configuration enables beam steering and acts as a deformable lens to focus the high radiation photons, ultrasonic waves or microwaves to desired depths and ensures selective killing of the cancerous cells. The beam focused inside the head phantom in FIG. 1B demonstrates the therapeutic capability of the therapy system 10. Thus, cancer therapy can be performed using the same setup without the patient leaving the table and hence without the need for any recalibration. This imaging cum therapy system also minimizes organ motion of both normal and tumor tissues caused by patient mobilization from imaging to therapy facility. The projection data measurement with flexible beam steering for localized radiation therapy makes the MEMS based imaging cum therapy system 10 conducive to the concurrent CT imaging and radiation therapy.

The MEMS based CT cum cancer therapy system has many advantages. During data collection, as the detector array 18 is fixed and the source array 12 alone is moved to a few predetermined positions, the system 10 configuration has minimal alignment and positioning errors associated with rotation or translation of the scanner as in existing CT equipment. The quasi stationary CT system 10 with hysteresis-free MMDM 16 enables faster data collection and minimal radiation or heat exposure. Even with LFOV, more projection data is easily collected using predetermined optimal mirror deflections. Unlike the contemporary CT systems, the performance of the image reconstruction algorithm is not constrained by the number of available projections as an enormous amount of projections can be measured with appropriate choice of mirror deflections. Thus, with this scanning arrangement, improved imaging results can be obtained for objects that restrict full view or equal distribution of the projection angle. The LFOV CT scan system 10 averts the need for a closed chamber and hence is patient friendly. The electrostatically driven continuous-membrane X-ray reflecting MMDM 16 consumes low power and thereby reduces the cost of the drive circuitry. The system 10 is also lightweight and can be packaged in integrated circuit packages with pin connections for external control. Advances in semiconductor fabrication also enable the inclusion of the system electronics into the MMDM 16. Thus, using a personal computer, precise and orderly control of X-ray source sweep, mirror deflections, data collection, transmission and X-ray beam focusing can be achieved.

In the next section, simulation results obtained using Kaczmarz algorithm for the MMDM based X-ray CT system are generated and compared with the classical X-ray CT methods. In all the simulations presented herein, due to lack of information on the physical properties of the X-ray reflective MEMS mirrors, Snell's law of reflection is used instead of Bragg's law of reflection.

For better visual perception, a variant of the commonly used "Shepp-Logan" head phantom is used in all the two-dimensional computer simulations. In the simulations, the X-ray scattering effects were neglected and only the primary X-ray path was considered for projection measurement.

During data collection, a fan beam X-ray source array 12 with 45 pencil beams was positioned at 14 locations along an arc and unique mirror shapes (flat, quadratic and cubic) were used. For each mirror shape, the transformation matrix A was assembled and the unique set of projection data collected with the mirror CT arrangement was used for two-dimensional image reconstruction. As used herein, a single iteration using Kaczmarz algorithm corresponds to obtaining projections on all the M hyperplanes, with M being the total number of unique projections.

Figure 5A:
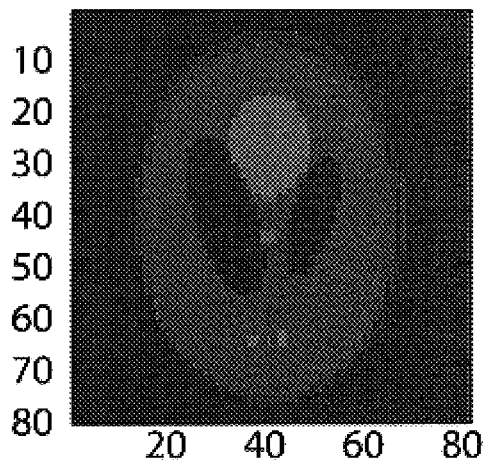
FIGS. 5A-D show Kaczmarz reconstruction results of the system of the present invention, with FIG. 5A illustrating an 81×81 modified Shepp-Logan phantom image, FIG. 5B illustrating reconstruction of the object at an 100th iteration, FIG. 5c illustrating reconstruction of the object at a 300th iteration, and FIG. 5C illustrating reconstruction of the object at a 500th iteration.
Figure 5B:
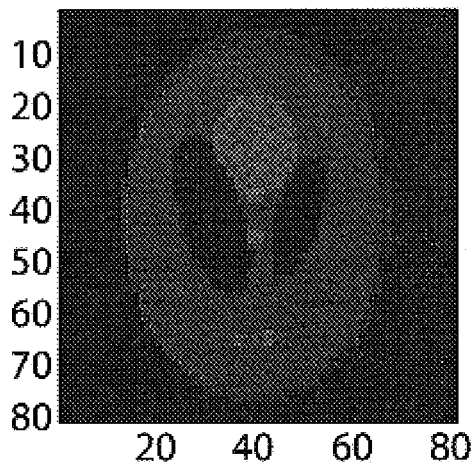
Figure 5C:
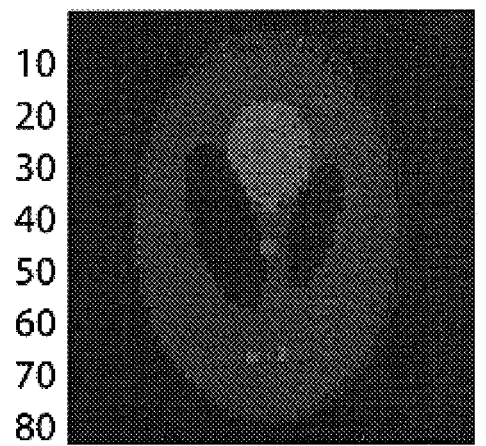
Figure 5D:
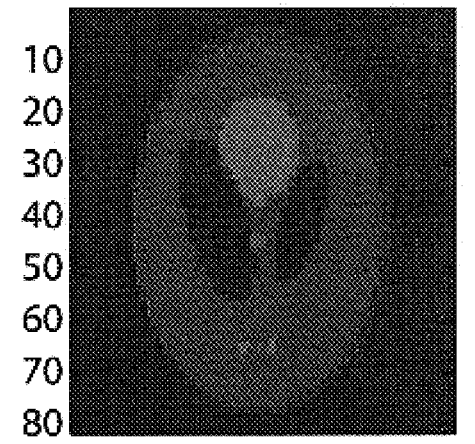
Figure 9A:
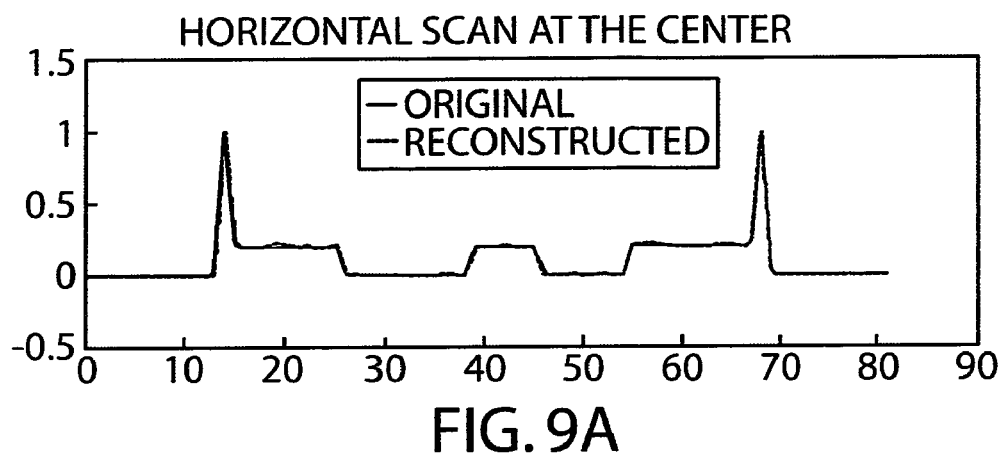
FIGS. 9A and 9B are a pair of graphs illustrating central line scans of the reconstructed phantom at 100th iteration for the MMDM based X-ray CT of the present invention, with FIG. 9A illustrating a horizontal line scan and FIG. 9B illustrating a vertical line scan.
Figure 9B:
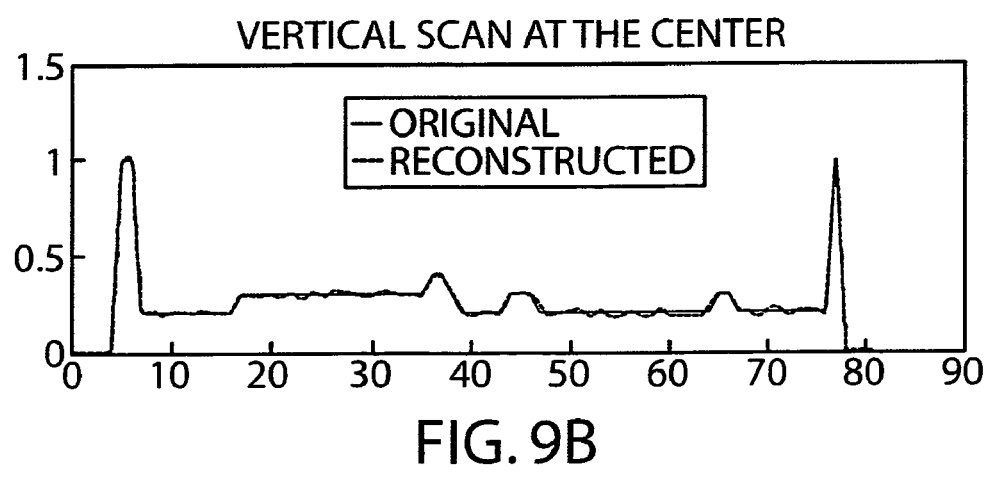
Figure 10A:
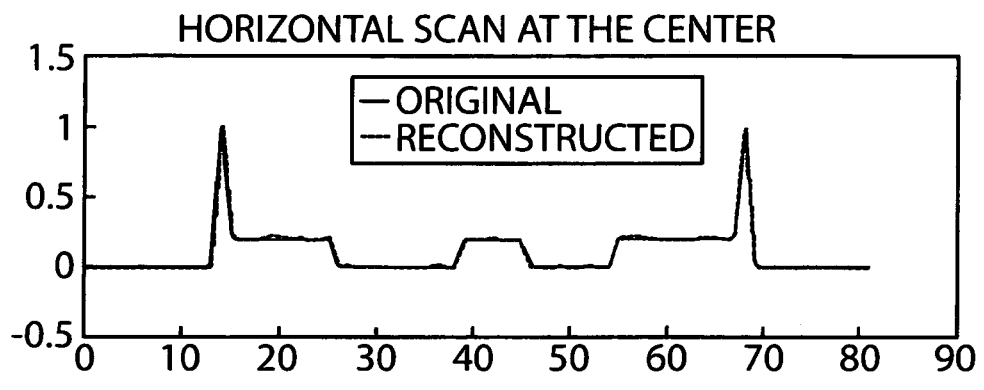
FIGS. 10A and 10B are a pair of graphs illustrating central line scans of the reconstructed phantom at 300th iteration for the MMDM based X-ray CT of the present invention, with FIG. 10A illustrating a horizontal line scan and FIG. 10B illustrating a vertical line scan.
Figure 10B:
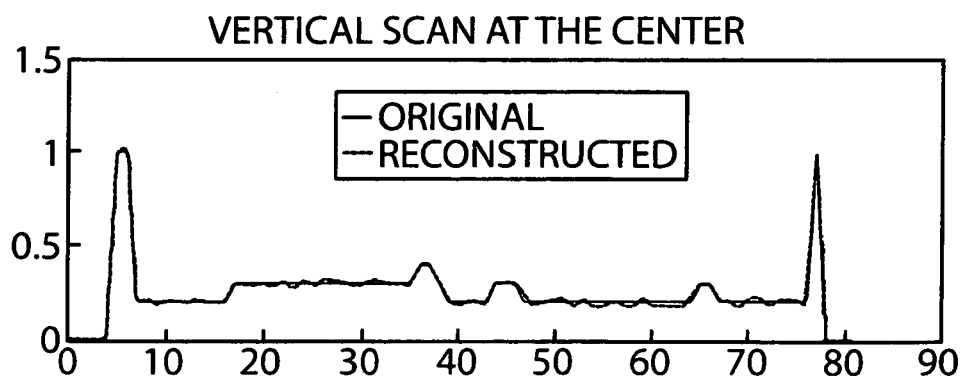

FIG. 5A shows the 81×81 Modified Shepp-Logan head phantom used in the simulation. Using 61 mirror shapes, 7039 unique projections were collected. FIGS. 5B-D show the reconstruction results obtained using the Kaczmarz algorithm at iteration 100, 300 and 500 respectively. At the 100th iteration, even though the reconstructed image has speckle noise, all the ellipses in the phantom were successfully recovered. With repeated projections, the quality of the reconstructed image improved with almost perfect reconstruction at the 500th iteration. FIGS. 9 and 10 show the horizontal and vertical line scans plotted along the center of the head phantom at the 100th and 300th iterations. A successive projection yielded a solution close to the true solution for our over-determined consistent system (M=7834, N=6561), a characteristic of Kaczmarz algorithm. Prior knowledge of the non-negative property of the spatial attenuation function f(x,y) and the boundary of the object being imaged were used to constrain the estimate during each projection. The computation time for a single iteration was approximately 1.03 s on a shared Sun Fire v880 server with 4×750 MHz UltraSPARC III processors.

In order to compare the reconstruction results with those obtained using classical X-ray CT techniques, a parallel beam X-ray CT system was simulated and projection data with 1° spacing in [00,1800) interval was collected. P pencil beams were used for L projection angles around the 81×81 Modified Shepp-Logan phantom image. A total of LP unique projections with L=180, P=90 were measured for Kaczmarz algorithm and L=180, P=117 were measured for image reconstruction using FBP algorithm. Both Kaczmarz (M=16200) and FBP (M=21060) reconstruction algorithms were implemented for the over-determined consistent linear system.

Figure 6A:
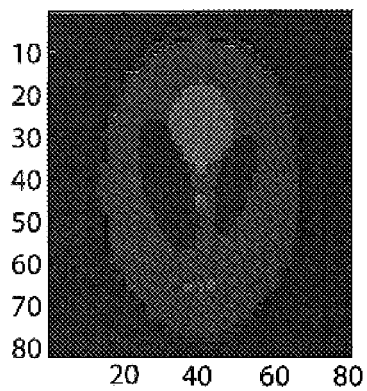
FIGS. 6A-F show CT reconstruction results of conventional CT methods, with FIG. 6A illustrating an 81×81 modified Shepp-Logan head phantom image, FIG. 6B illustrating a Kaczmarz reconstruction of the object at an 60th iteration, FIG. 6C illustrating Kaczmarz reconstruction of the object at an 300th iteration, FIG. 6D illustrating a filtered back projection reconstruction with Ram-Lak filter and spline interpolation of the object, FIG. 6E illustrating a filtered back projection reconstruction with Ram-Lak filter and spline interpolation of the object at an 60th iteration, and FIG. 6F illustrating a filtered back projection reconstruction with Ram-Lak filter and spline interpolation of the object an 300th iteration.
Figure 6B:
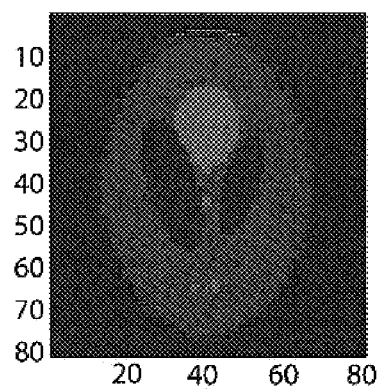
Figure 6C:
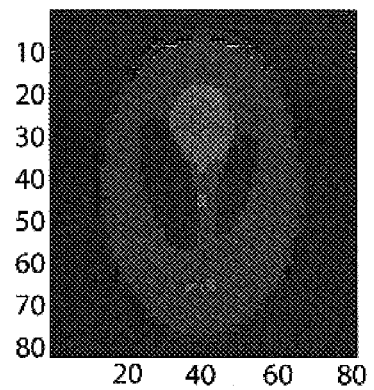
Figure 6D:
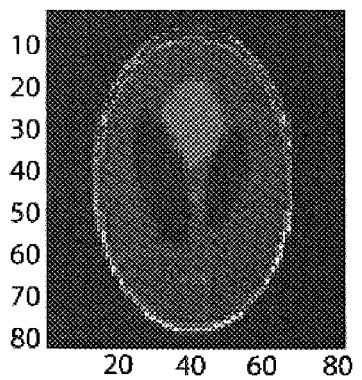
Figure 6E:
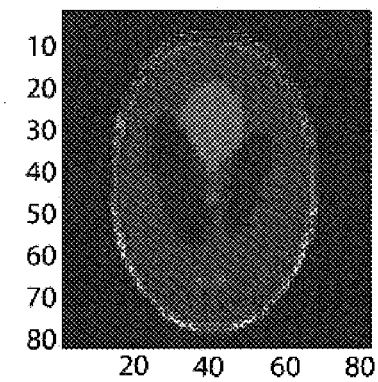
Figure 6F:
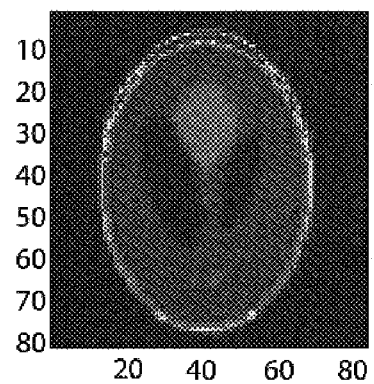

FIGS. 6B-6C show the reconstruction result at the 60th and 300th iterations obtained with Kaczmarz algorithm results for the classical X ray CT method. For the same number of iterations, the reconstruction result in FIGS. 6C and 5C are comparable demonstrating the merit of the X-ray CT system 10 of the present invention. For the conventional X ray CT, projection data was collected for the equally distributed projection angle in [00,1800) with 1° spacing unlike the LFOV in the scan configuration of the present invention. With the contemporary CT scan geometries, it is not possible to reconstruct the two-dimensional cross section accurately with limited angle or limited-view data. FIGS. 6D-6F shows reconstruction results obtained using the FBP algorithm for different filtering and interpolation choices. The FBP method smears the projections back into the image space hence, despite fast implementation; the reconstruction result evidently lacks in details and requires post processing for image enhancement.

For ease of computation, all simulations for conventional CT use parallel beam geometry. For perfect reconstruction, the most commonly used FBP algorithm in the existing CT system requires equi-spaced, equi-angular scan rotation in [0,180) interval for parallel beam geometry and [0,360) interval for fan beam geometry. Thus, for a fair comparison of the reconstruction results, equi-spaced equi-angular X-rays with 1° spacing in [00,1800) interval was used for conventional CT simulations.

Next, to demonstrate the merit of the approach (A) with the existing X-ray CT techniques using iterative methods (B) and FBP (C); limited-angle scenarios prevalent in many real time applications were simulated. Projection data was collected for parallel beam X-ray CT system using equally distributed projection angle in [450,1350] interval with 1° separation and image reconstruction was carried out using algorithms B and C. For limited-view simulation, the head phantom in FIG. 6A was used and 90×90 and 90×117 projections were collected for B and C respectively.

FIGS. 7D-7F shows the reconstruction results of algorithm C for Ram-Lak, Hamming and Shepp-Logan filters with spline interpolation. As FBP involves back projecting the filtered projections collected at equally distributed angles over 1800 or 3600 into the image space, the reconstruction results suffer severely because of limited-view projection data and lacks the accuracy required in medical applications. FIGS. 7B-7C show reconstruction results obtained using algorithm B at the 60th and 250th iterations. As expected, the iterative reconstruction results for limited-view X-ray CT are acceptable since the iterative method does not require full view projection measurements. In the simulations for the mirror-based approach, the fan beam source array was positioned on a circular arc within 450 and 1350 and the position of the MMDM 16 and the detector array 16 were fixed. Hence, our reconstruction results in FIGS. 5B-5D in a sense are for a limited view projection measurement. For the limited-view conventional X ray CT simulation, parallel beam X-ray projections were measured with 1° separation in [450, 1350] interval requiring 91 source-detector positions during projection measurement. In contrast, in the CT system 10 of the present invention, projections were collected only for 14 pre-determined source locations with a fixed mirror-detector arrangement.

Figure 8A:
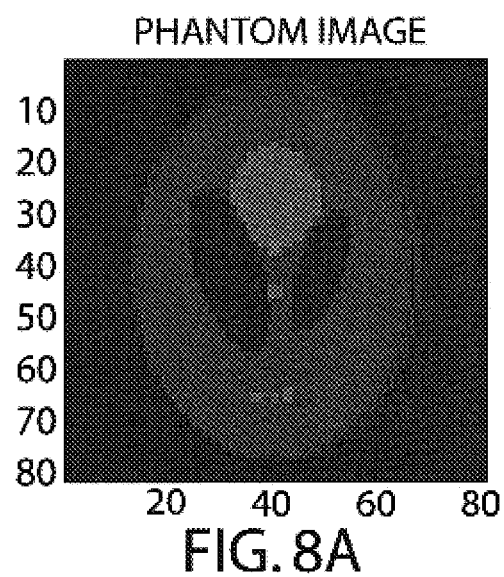
FIGS. 8A-B show Kaczmarz reconstruction for conventional CT with LFOV scan configuration similar to the MMDM based CT technique, with FIG. 8A illustrating an 81×81 modified Shepp-Logan head phantom image and FIG. 8B illustrating a Kaczmarz reconstruction of the object at a 200th iteration for a parallel beam X-ray source.
Figure 8B:
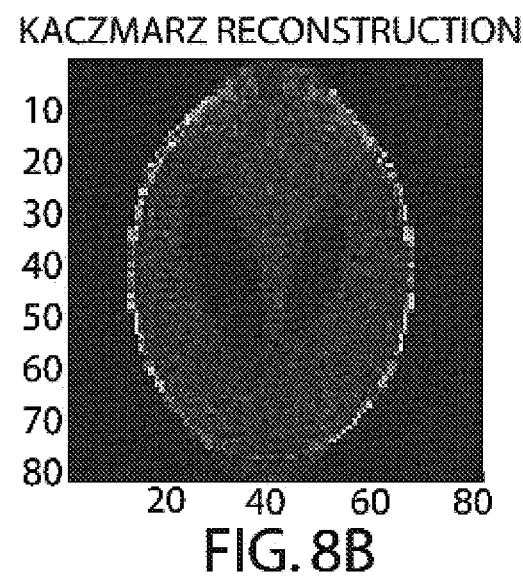

To evaluate the efficacy of the conventional CT using iterative algorithms, simulations were carried out for 15 projection angles equally spaced in [450, 1350] interval, a scenario similar to the scan configuration in the MEMS based CT system 10 of the present invention. The 81×81 head phantom was used and 90×15 projections were collected using parallel beam X-ray source. FIG. 8B shows the reconstructed image after the 200th iteration for the consistent underdetermined linear system. The reconstruction result is apparently poor and does not improve much with additional iterations. Even though the scan configuration was almost the same with the mirror based approach of the present invention, more projections were easily obtained using a wise choice of mirror shapes. The mirror 16 compensated the limited source movement and yielded superior image reconstruction. During the simulations, projection data for the conventional CT system was also collected using fan beam source with the source array and detector array positions used in the MEMS based CT system of the present invention. With the conventional CT system, the projection data measured using the MEMS based scan geometry was insufficient to reconstruct the two-dimensional image and hence the reconstruction result is not presented. A detailed comparison of the simulation results obtained for different CT systems reveals a promising future for the deformable mirror based CT technique in noninvasive imaging.

Accordingly, a new design of an X-ray CT cum tomotherapy system using X-ray reflecting deformable mirrors 16 for efficient projection data measurement and radiation therapy has many improvements over prior art systems. The simulated reconstruction results are comparable to the full view classical X-ray CT reconstructions and are superior to those obtained with limited-view CT. Even though the simulations were carried out using Snell's law of reflection, the approach will work well for Bragg's law of reflection and with a proper choice of reflective coating, projections can be measured even for almost normally incident X-rays. The idea underlying the MMDM based X-ray CT cum radiation therapy system 10 of the present invention is not only valid for imaging solid opaque objects using X-ray CT but is equally valid for imaging diffracting penetrable objects as in ultrasound and microwave imaging modalities. It is contemplated that the system 10 can be used for microwave medical imaging and therapy. One of the major advantages of the system 10 is related to the fact that the same system could be used for imaging as well as radiation therapy, thereby minimizing collateral damage to neighboring tissue during therapy. Additionally, the open-ended nature of the design is a huge benefit to claustrophobic patients and young children.

Figure 2:
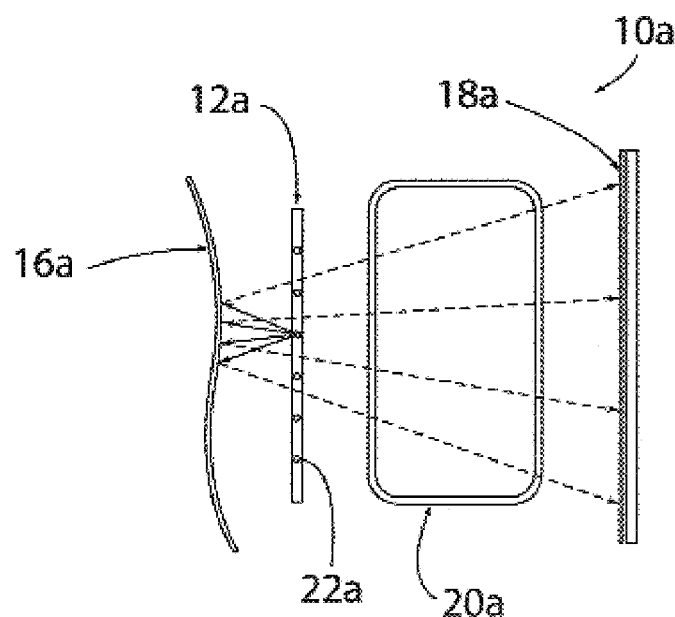
FIG. 2 is a schematic representation of a second embodiment of a tomographic imaging system of the present invention.

The reference numeral 10a (FIG. 2) generally designates another embodiment of the present invention, having a second embodiment for the system. Since system 10a is similar to the previously described system 10, similar parts appearing in FIG. 1 and FIG. 2, respectively, are represented by the same, corresponding reference number, except for the suffix "a" in the numerals of the latter. FIG. 2 shows the schematic diagram of the cross-sectional view of the proposed MMDM based X-ray CT system 10a for cargo container screening. The system 10 comprises a fan beam source array 12a and a linear detector array 18a positioned on either side of the cargo container 20a. The continuous-membrane deformable X-ray reflecting mirror 16a is placed on the same side as the source array 12. In this CT scan configuration, the detector array 18a and the X-ray reflective MMDM 16a device remain fixed and the fan beam X-ray source array 12a is moved to few predetermined locations for projection measurement.

During data acquisition, X-ray projections are measured for different mirror deflections for each source location. The mirror shapes are controlled by applying appropriate predetermined potential distributions between the substrate and the actuator structure as discussed above in regard to FIG. 3. Depending on the mirror deformation, the incident high energy X-rays get diverted along a path determined by Bragg's law of reflection and gets detected at the linear detector array. The size of the cargo container and time constraints prohibits multi-view scanning of the containers and the limited-field-of-view (LFOV) imaging in conventional computed tomography yields images with poor resolution. Any missed detection during screening is fraught with problems. Thus, a screening technique with high resolution is desired. Unlike contemporary CT systems, the MEMS based CT system 10 offers far more degrees of freedom even with a limited field-of-view (LFOV). A voluminous and information-rich projection data set can be collected using a multitude of membrane shapes.

In the next section, simulation results obtained using the Kaczmarz algorithm for the MMDM based X-ray CT system 10 are presented. In all the simulations, due to lack of information on the physical properties of the X-ray a reflective MEMS mirror 16a, Snell's law of reflection was used instead of Bragg's law.

In the simulation, high energy X-rays with monochromatic radiation was assumed and only the primary X-ray path was considered. During projection measurement, a fan beam X-ray source array 12a with 60 pencil beams was positioned at 14 locations and unique mirror shapes were used. For each mirror shape, the projection matrix A was assembled and the unique set of projections was collected using the mirror CT arrangement. The X-ray attenuation coefficient of the phantom cargo container was reconstructed using the iterative equations (2)-(4). In our discussions, a single iteration using the Kaczmarz algorithm corresponds to obtaining projections on all the M hyperplanes, with M being the total number of unique projections and N being the dimensionality of each hyperplane.

Figure 11A:
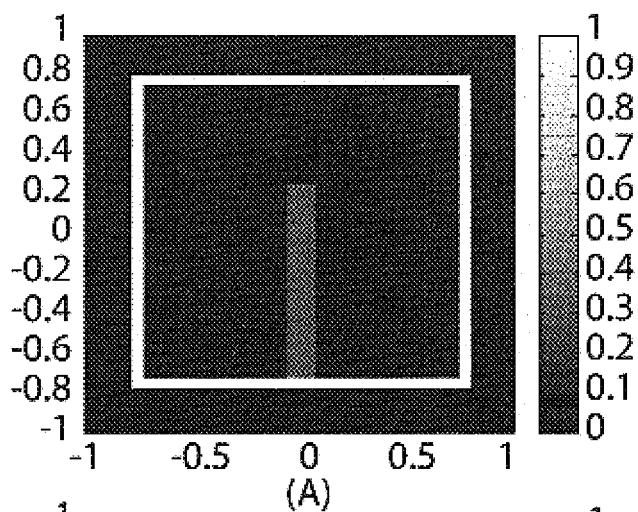
FIGS. 11A-C illustrate phantom of a cargo container (FIG. 11A), the cargo container's reconstructed image at 50th iteration (FIG. 11B), and the cargo container's reconstruction error at 50th iteration (FIG. 11C).
Figure 11B:
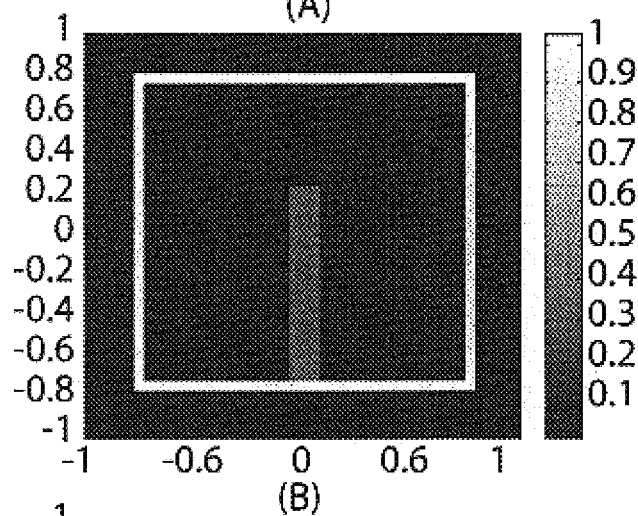
Figure 11C:
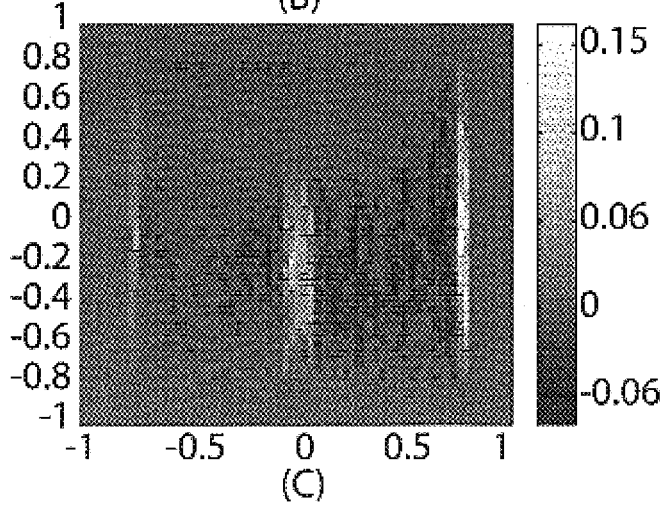
Figure 12A:
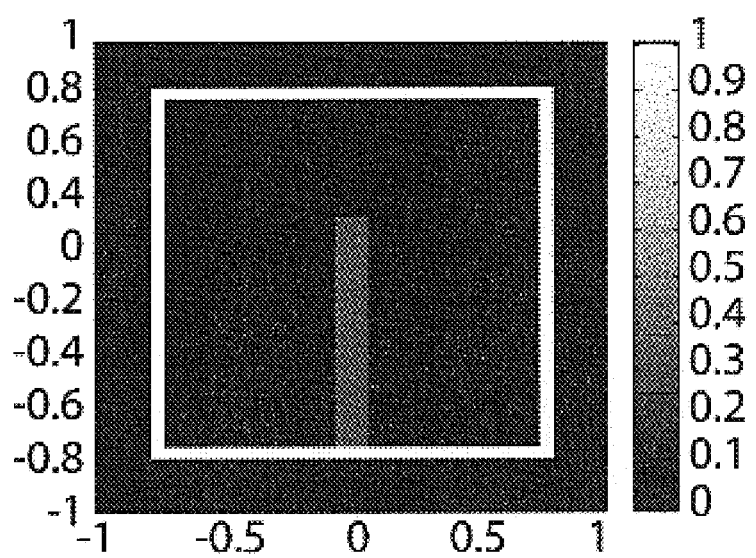
FIGS. 12A-B illustrate the cargo container's reconstructed image at 100th iteration (FIG. 12A) and the cargo container's reconstruction error at 100th iteration (FIG. 12B).
Figure 12B:
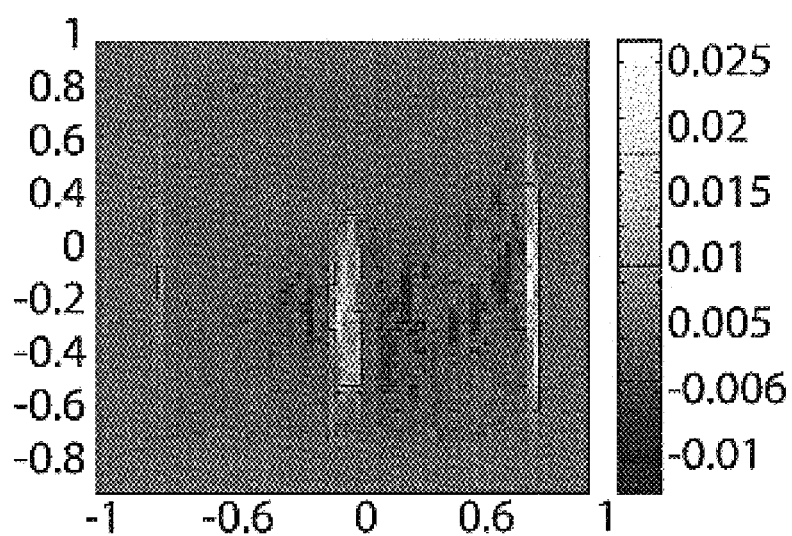

FIG. 11A shows a 73×73 cargo container phantom used in the simulation. The phantom consists of a steel container with an aluminum rod at the center. In the simulation, the linear attenuation coefficient of steel and aluminum at 3 MeV were calculated using the tables from the National Institute of Standards and Technology in Gaithersburg, Md., and 10328 unique projections were collected for image reconstruction. In the simulation, the attenuation coefficients of the phantom were normalized to vary between [0, 1]. FIGS. 11B-11C show the reconstruction results obtained using the Kaczmarz algorithm at the 50th iteration. FIG. 11C shows the error in reconstruction at the 50th iteration. At the 50th iteration, the boundaries of the container and the aluminum rod in FIG. 11B match very well with the phantom in FIG. 11A. FIGS. 12A-12B shows the reconstructed image and the reconstruction error at the 100th iteration. With repeated projections, the quality of the reconstructed image at the 100th iteration improves yielding a solution close to the true solution for the over-determined consistent system with M=10328 and N=5329 Prior knowledge of the non-negative property of the spatial attenuation function f(x,y) and the boundary of the phantom were used to constrain the estimate during each projection. The computation time for a single iteration was approximately 0.96 s on a shared Sun Fire v880 server with 4×750 MHz UltraSPARC III processors.

Accordingly, a new design of an X-ray CT system 10a using X-ray reflecting deformable mirrors 16a for efficient projection data measurement has been presented and initial results obtained with a cargo container containing a phantom were presented. The simulated reconstruction results reveal a promising future for the deformable mirror based CT systems 10a for non-intrusive imaging of cargo containers at ports of entry. Even though the simulations were carried out using Snell's law of reflection, the approach will work well for Bragg's law of reflection and with a proper choice of reflective coating, projections can be measured even for almost normally incident X-rays.

Figure 13:
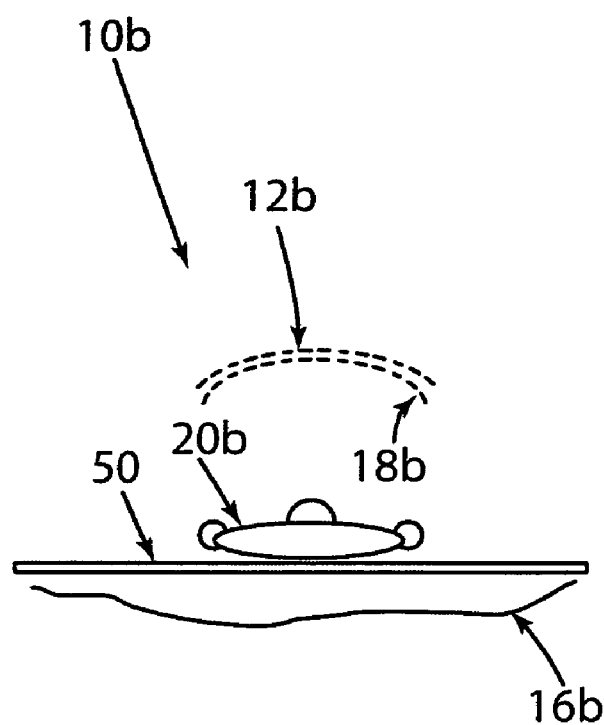
FIG. 13 is a schematic of a third embodiment of a tomographic imaging system of the present invention.
Figure 13A:
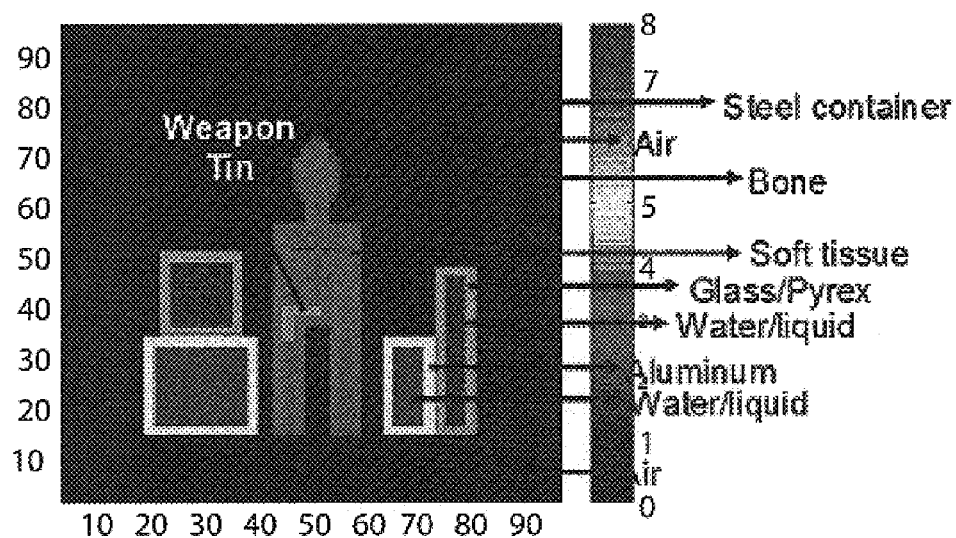
FIGS. 13A-H illustrates a phantom of a cargo container (FIG. 13A), the cargo container's reconstructed image at 1st iteration (FIG. 13B), the cargo container's reconstruction image at 100th iteration (FIG. 13C), the cargo container's reconstruction image at 200th iteration (FIG. 13D), the cargo container's reconstruction image at 400th iteration (FIG. 13E), the cargo container's reconstruction error at 100th iteration (FIG. 13F), the cargo container's reconstruction error at 200th (FIG. 13G), and the cargo container's reconstruction error at 400th iteration (FIG. 13H).

FIG. 13A shows a 97×97 cargo, container phantom used in the simulation. The phantom consists of a steel container with a glass or borosilicate container having water or a liquid therein, an aluminum container having water or a liquid therein, and a person having soft tissue, bone tissue and a weapon comprising tin therein. In the simulation, the linear attenuation coefficient of steel, tin, aluminum, bone, soft tissue, water/liquid and glass/borosilicate at 3 MeV were calculated using the tables from the National Institute of Standards and Technology in Gaithersburg, Md., and 9714 unique projections with 39 different mirror shapes were collected for image reconstruction. Table 1 below shows the linear attenuation coefficient of the elements at 3 MeV (1/m).

TABLE 1

| Element | Linear attenuation coefficient @ 3 MeV (1/m) |
| --- | --- |
| Steel | 28.32 |
| Tin | 26.94 |
| Aluminum | 9.56 |
| Bone | 7.19 |
| Soft tissue | 3.931 |
| Water/liquid | 3.969 |
| Glass, Borosilicate (Pyrex) | 8.05 |

Figure 13B:
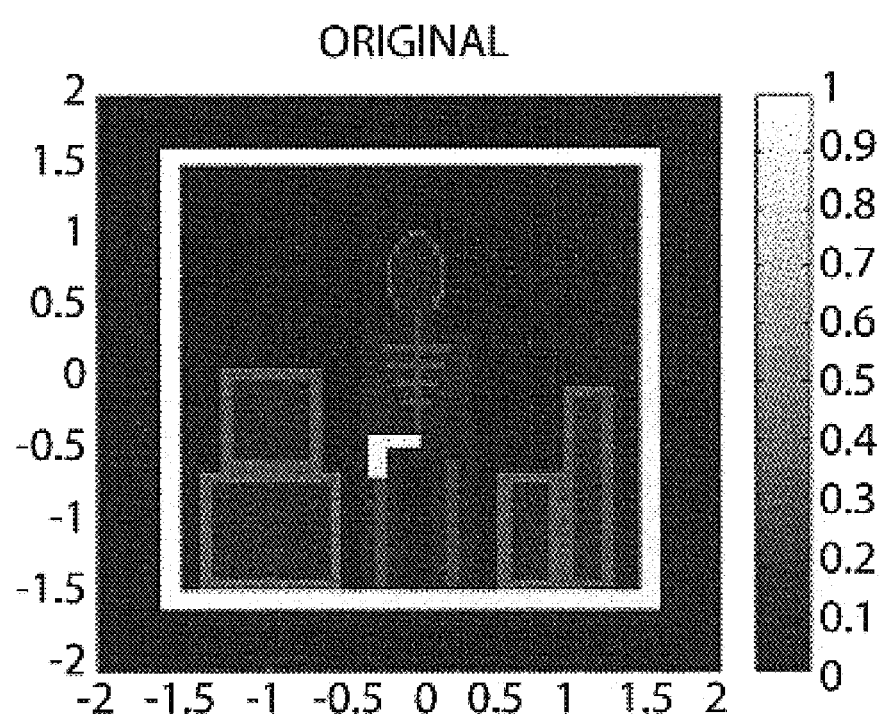
Figure 13C:
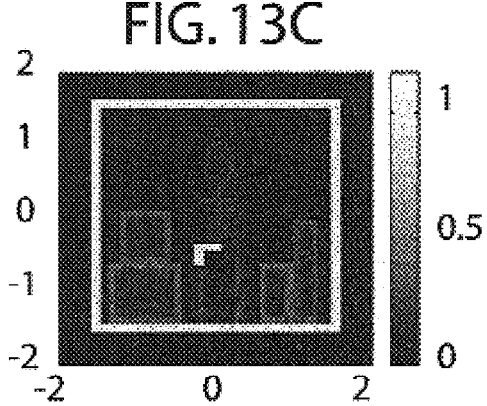
Figure 13F:
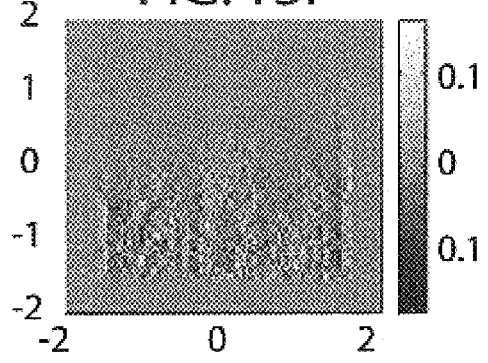
Figure 13D:
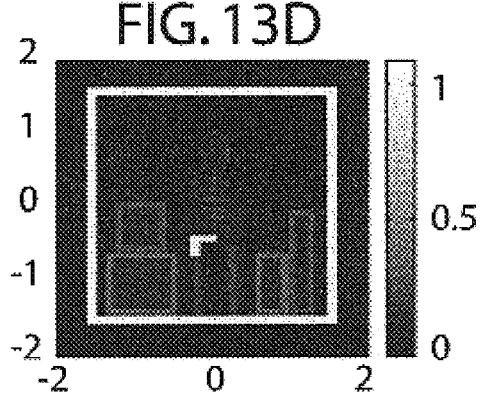
Figure 13G:
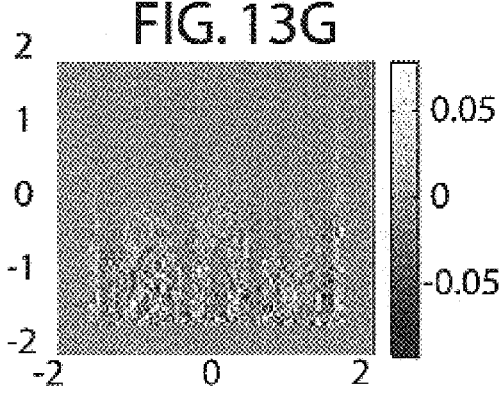
Figure 13E:
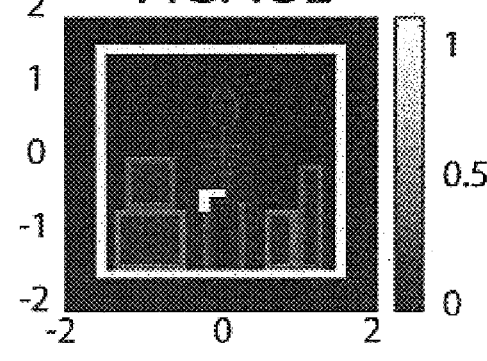
Figure 13H:
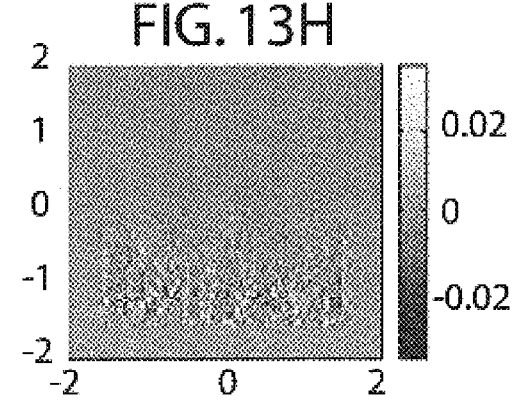

In the simulation, the attenuation coefficients of the phantom were normalized to vary between [0, 1]. FIG. 13B shows the reconstruction results obtained using the Kaczmarz algorithm at the $1^{st}$ iteration. FIGS. 13C-13E show the error in reconstruction at the $100^{th}$ iteration, $200^{th}$ iteration and $400^{th}$ iteration, respectively. FIGS. 13F-13H show the error in reconstruction at the $100^{th}$ iteration, $200^{th}$ iteration and $400^{th}$ iteration, respectively. At the $100^{th}$ iteration, $200^{th}$ iteration and $400^{th}$ iteration, the boundaries of the container and elements therein in FIGS. 13C-13E match very well with the phantom in FIG. 13A. With repeated projections, the quality of the reconstructed image at the $400^{th}$ iteration improves yielding a solution close to the true solution for the overdetermined consistent system with M=10328 and N=5329. Prior knowledge of the non-negative property of the spatial attenuation function f(x,y) and the boundary of the phantom were used to constrain the estimate during each projection. The computation time for a single iteration was approximately 0.96 s on a shared Sun Fire v880 server with 4×750 MHz UltraSPARC III processors.

The reference numeral 10b (FIG. 13) generally designates another embodiment of the present invention, having a second embodiment for the system. Since system 10b is similar to the previously described system 10, similar parts appearing in FIG. 1 and FIG. 13, respectively, are represented by the same, corresponding reference number, except for the suffix "b" in the numerals of the latter. FIG. 13 shows the schematic diagram of the cross-sectional view of the proposed MMDM based X-ray CT system 10b which comprises a fan beam source array 12b and an arcuate detector array 18b positioned on one side of the patient 20b. The patient 20b lays on a flat surface or bed 50 and the continuous-membrane deformable X-ray reflecting mirror 16b is hidden beneath the patient 20b and, consequently, the patient is unaware of the mirror's presence. The source array 12b is located far above the patient 20b and the rays from the source array 12b pass through the patient 20b, get reflected by the mirror 16b and pass through the patient 20b once again to their path to the detector array 18b. The shape of the mirror 16b is changed continuously and at each step, the response of the detector array 18b is recorded. The numerical algorithm based on Kaczmarz's approach as discussed above is used to reconstruct the tomogram of the patient from the data collected by the detector array 18b.

Figure 14:
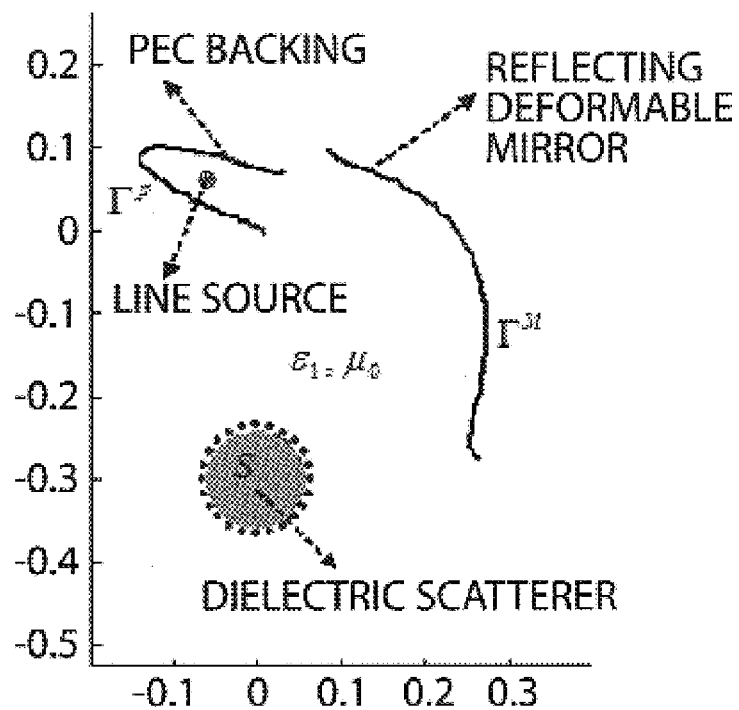
FIG. 14 is a schematic representation of a fourth embodiment of a tomographic imaging system of the present invention.

FIG. 14 generally designates another embodiment of the present invention, having a fourth embodiment for the system. The fourth embodiment of the system is used in active microwave imaging (or tomography) systems involving reconstruction of a spatial distribution of electrical properties inside of a penetrable dielectric object using multi-view field measurements. The microwave imaging system preferably employs a continuously deformable mirror and a single fixed transmitter. The imaging system is capable of generating a multitude of field measurements to recover a spatial distribution of unknown permittivity inside the penetrable dielectric object.

FIG. 14 is a schematic diagram for the microwave imaging system for inverse scattering applications. The microwave imaging system preferably comprises a continuously deformable mirror, a fixed highly directional transmitter antenna illuminating a surface of the mirror, and a circular array of receiver antennas surrounding a penetrable dielectric scatterer. In this microwave imaging system, a field emitted by the transmitter antenna is reflected at a surface of the mirror and is steered towards the dielectric scatterer. The direction of arrival of an incident field on the scatterer is controlled by adaptively changing the shape of the mirror. During data acquisition, a total field maintained by the scatterer is measured at the receiver antennas for a predetermined set of unique mirror shapes. As discussed in more detail below, measurements acquired for all predetermined mirror shapes are used in an inversion algorithm to determine the spatial distribution of electrical properties of the penetrable dielectric object.

Feasibility of the imaging system was analyzed using two-dimensional numerical simulations. Mathematical treatment of a forward problem for field measurements solves the scalar Helmholtz wave equation for TMz polarization. In the simulation, the numerical model treats the scatterer as an arbitrarily shaped inhomogeneous dielectric cylinder with infinite dimension along the z-axis. The mirror is approximated by a perfectly conducting arbitrarily shaped metal strip and the directional electromagnetic source is modeled as an infinitely long line current source enclosed within an infinitely long perfectly conducting wedge with rounded vertices.

The total field maintained by the scatterer satisfies the scalar Helmholtz wave equation, $$(\nabla^2 + k_d^2)\phi(\vec{\rho}) = 0, \vec{\rho} \in S \qquad (5)$$

inside the scatterer and the boundary integral equation, $$\phi(\vec{\rho}) = J_z^{im} \otimes G_{2D} - \frac{\omega\mu_0}{4}\int_{\Gamma^P} J_z^P(\vec{\rho'}) G_{2D}(k_1|\vec{\rho} - \vec{\rho'}|) d\Gamma' \qquad (6)$$

$$\oint_{\Gamma^S} \phi(\vec{\rho'}) \partial'_n G_{2D}(k_1|\vec{\rho} - \vec{\rho'}|) d\Gamma' -$$

$$\oint_{\Gamma^S} \partial'_n \phi(\vec{\rho'}) G_{2D}(k_1|\vec{\rho} - \vec{\rho'}|) d\Gamma' - \frac{\omega\mu_0}{4}\int_{\Gamma_M} J_z^m(\vec{\rho'}) G_{2D}(k_1|\vec{\rho} - \vec{\rho'}|) d\Gamma'$$

outside the scatterer. In (5), $\nabla^2 = (\partial^2/\partial x^2 + \partial^2/\partial y^2)$ is the Laplacian operator, $k_d$ is the complex wave number inside the scatterer, $\phi(\bar{\rho})$ is the scalar TMz polarized field and $\bar{\rho}$ is the two dimensional position vector. In (6), $J_z^{im}$ represents the impressed line current density, $J_z^P$, $J_z^m$ represent the induced current densities on a photoelectric wedge and deformable mirror respectively, $k_1$ is the wave number in the background medium and $G_{2D}$ is the scalar 2D Greens function. The field inside the scatterer is solved using the finite element method and the field anywhere external to the dielectric and photoelectric scatterers are given by the boundary integral equation (6). The finite element boundary integral equations are solved simultaneously with boundary conditions, $$\phi(\bar{\rho})=0; \bar{\rho}\epsilon\Gamma^M,\Gamma^P \qquad (7)$$

for the unknown field and induced current densities. With the knowledge of the field and induced current densities, field measurements anywhere outside is computed using (6). Prior to permittivity inversion, the finite element boundary integral equation is solved for different mirror shapes for the field maintained by the dielectric scatterer at the receiver locations.

Figure 15:
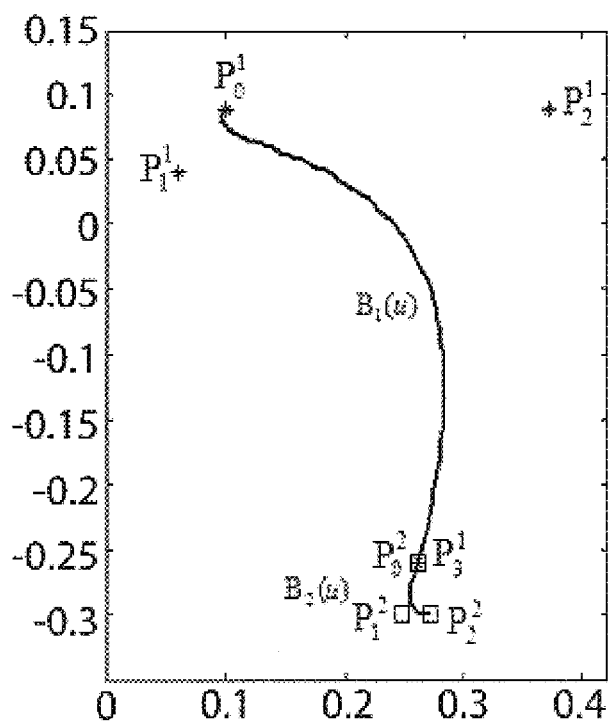
FIG. 15 illustrates an example of a higher order Bezier curve represented using a lower order Bezier curves.

The efficacy of the proposed imaging system preferably finds smooth mirror shapes that can steer the incident field towards the scatterer. The mirror surface in the two-dimensional simulations is represented using the generalized Bezier parametric curve of the form, $$f(u) = \sum_{k=0}^{N} p_k b_{k,N}(u) \qquad (8)$$

where $p_k$ are the N+1 control points of the $N^{th}$ order Bezier-basis Bernstein polynomials, $$b_{k,N} = \binom{N}{k} u^k (1-u)^{N-k} \qquad (9)$$

that blend the control points to form the Bezier curve. FIG. 15 illustrates an example of a higher order curve represented using lower order Bezier curves. In the simulations, corners of the deformable mirror were rounded using lower order Bezier curve to avoid undesired scattering.

Of the multitude possible mirror shapes f(u), a predetermined set of shapes $f_p(u)$ is selected for permittivity inversion where $1 \leq p \leq P$. During mirror selection, for each mirror shape, the total field inside the imaging region in an absence of the scatterer is computed by solving (6) and (7). For each mirror shape, features such as energy inside the imaging region $E_i^{doi}$, energy in the shadow region $E_i^{shad}$ and the correlation $\rho_{ij}^{doi}$, between the fields inside the imaging region S for the ith and jth mirror shapes are computed. The features thus computed are used to identify mirror shapes that satisfy the criteria, $$\max\{E_i^{doi} / E_i^{shad}\} \qquad (10)$$

$$\min\{\rho_{ij}^{doi}\}; 1 \leq i, j \leq P, i \neq j$$

The mirror shapes that satisfy the above criteria ensures maximum energy coupling towards the scatterer with minimum energy leakage due to creeping waves. This method can also be used to determine shapes of the deformable mirrors in any system described herein.

The total field measured in the presence of the scatterer for the optimal mirror shapes are used in the inversion algorithm. Permittivity inversion is a nonlinear problem that aims to find an optimal solution to the minimization problem, $$\varepsilon^{opt} = \arg\min \frac{1}{2} \|\phi^m(\vec{\rho}_m, \varepsilon) - \phi^c(\vec{\rho}_m, \varepsilon)\|^2, \qquad (11)$$

In (11), $\phi^m(\bar{\rho})$ corresponds to the field measurements surrounding the scatterer computed using the actual permittivity distribution and $\phi^c$ contains the field measurement computed in the iterative inversion process for the estimated permittivity. Linearization of the Taylor series expansion of the field about the solution yields an equation of the form, $$\frac{d\phi(\varepsilon)}{d\varepsilon}\Delta\varepsilon = \phi(\varepsilon^{sol}) - \phi(\varepsilon) \qquad (12)$$

Starting with an initial estimate, the total field $\phi(\epsilon)$ and the Jacobian $d\phi(\epsilon)/d\epsilon$ are computed for each mirror shape using (5)-(7). The incremental quantity $\Delta\epsilon$ in (12) yields the permittivity estimate for the next iteration, $$\epsilon^{n+1}=\epsilon^n+\alpha\Delta\epsilon; \alpha>0 \qquad (13)$$

The inversion process is iterated until the measurement error is preferably below the tolerance level or the permittivity estimate has not reached a stable solution. Equation (12) in inverse scattering applications yields an unstable solution due to the ill-conditioned nature of the Jacobian matrix particularly when the initial estimate is far away from the true solution. The instability in (12) is minimized by solving the regularized problem, $$[J^T J + \lambda L^T L]\Delta\epsilon = \phi(\epsilon^{sol}) - \phi(\epsilon), \lambda > 0 \qquad (14)$$

where J is the rectangular Jacobian matrix $d\phi(\epsilon)/d\epsilon$, L is an operator that incorporates the prior information and penalizes unstable or noisy solution and $\lambda$ is the regularization parameter determined empirically. When L equals the identity matrix, the zero$^{th}$ order regularization problem is solved.

Figure 16:
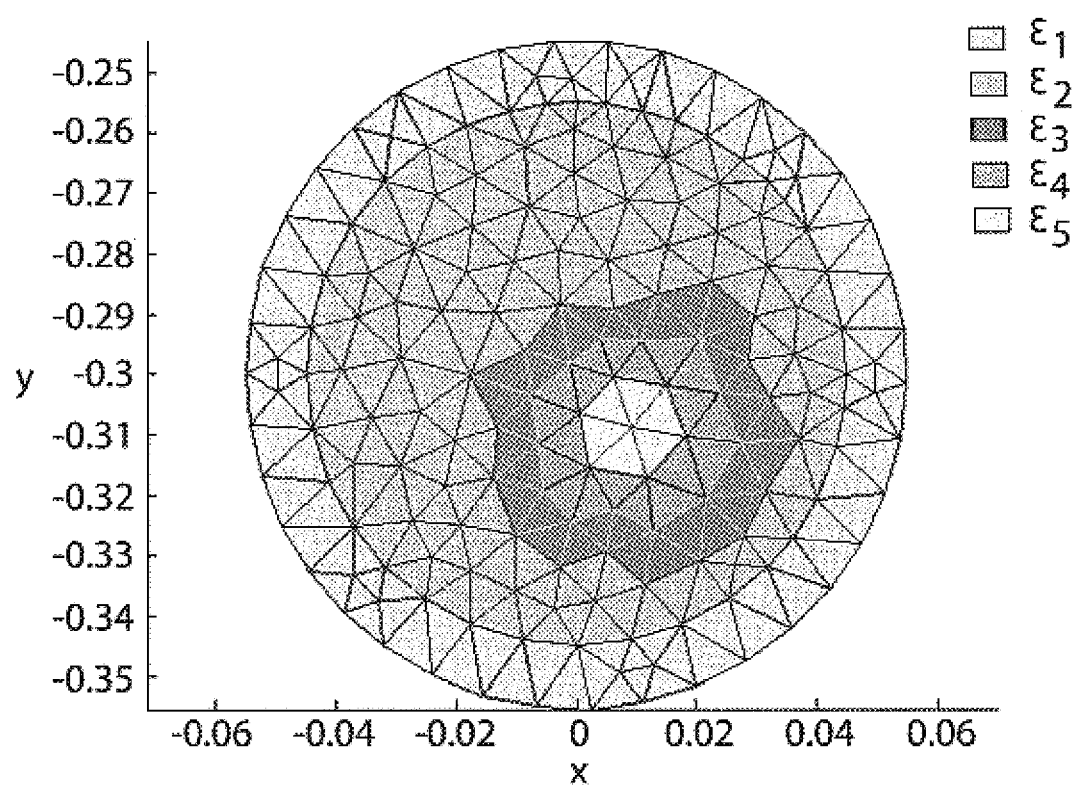
FIG. 16 illustrates a two-dimension mesh of an inhomogeneous dielectric scatterer with background permittivity $\epsilon 1$.
Figure 17A:
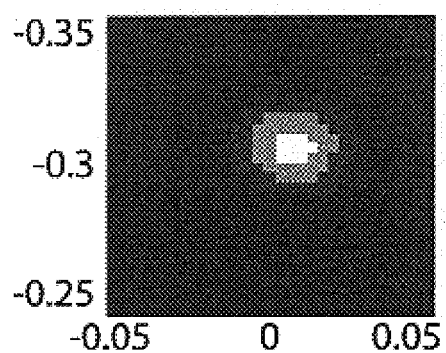
FIGS. 17A-17H illustrate tomographic reconstructions using the fourth embodiment of the tomographic imaging system of the present invention, with FIG. 17A illustrating a reconstruction at a $68^{th}$ interation with $\epsilon'$ of true distribution, FIG. 17B illustrating a reconstruction at a $68^{th}$ interation with $-\epsilon''$ of true distribution, FIG. 17C illustrating a reconstruction at a $68^{th}$ interation with $\epsilon'$ for eight mirror shapes, FIG. 17D illustrating a reconstruction at a $-68^{th}$ interation with $-\epsilon''$ for eight mirror shapes, FIG. 17E illustrating a reconstruction at a $68^{th}$ interation with $\epsilon'$ for twelve mirror shapes, FIG. 17F illustrating a reconstruction at a $68^{th}$ interation with $-\epsilon''$ for twelve mirror shapes, FIG. 17G illustrating a reconstruction at a $68^{th}$ interation with $\epsilon'$ for sixteen mirror shapes, and FIG. 17H illustrating a reconstruction at a $68^{th}$ interation with $-\epsilon''$ for sixteen mirror shapes.
Figure 17B:
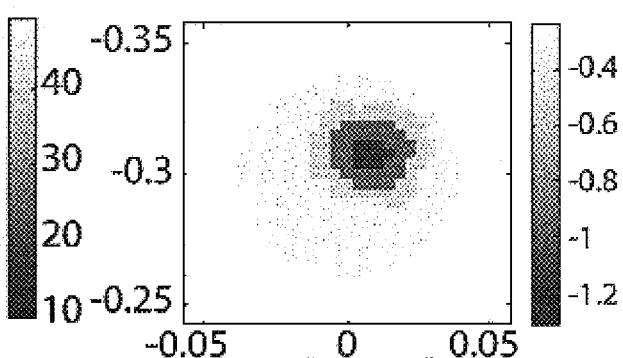
Figure 17C:
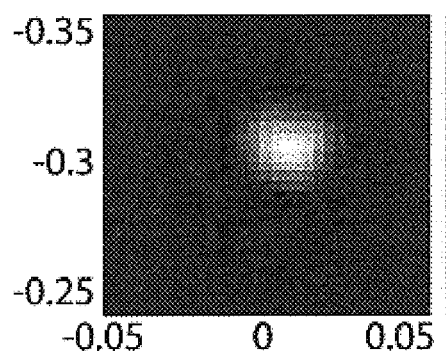
Figure 17D:
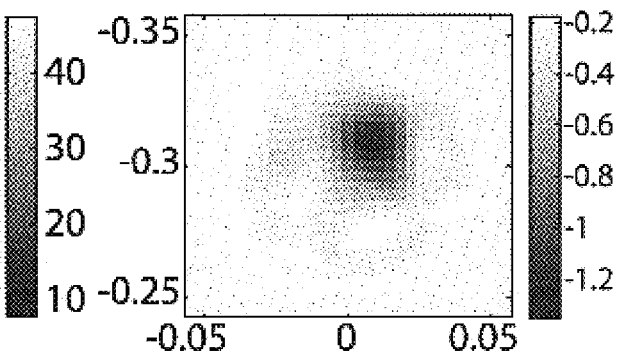
Figure 17E:
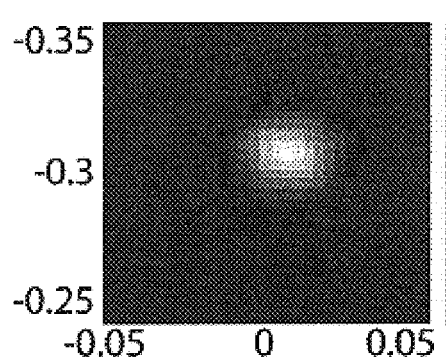
Figure 17F:
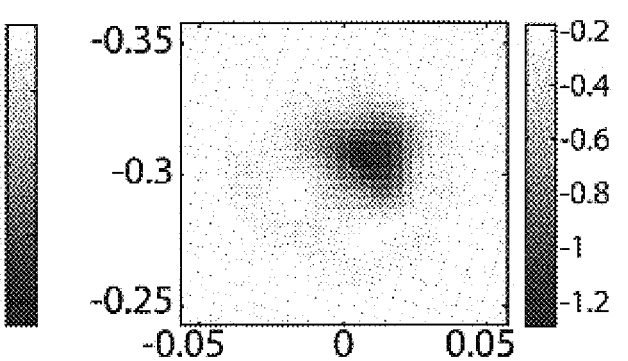
Figure 17G:
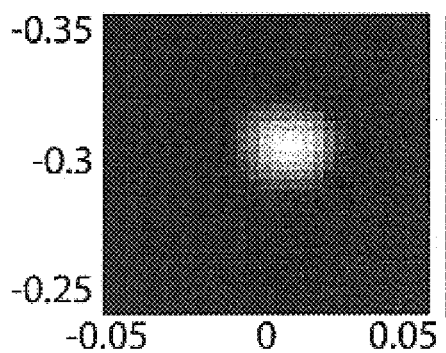
Figure 17H:
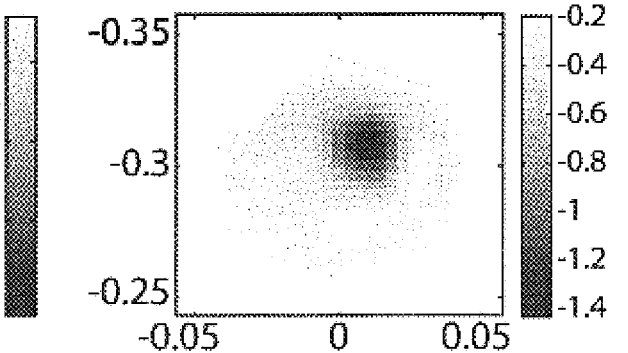
Figure 18A:
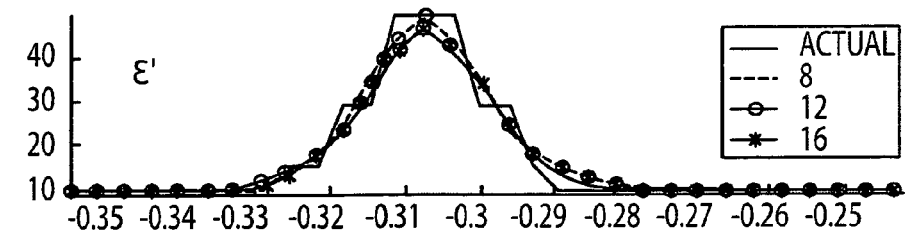
FIGS. 18A-18D illustrate a comparison of permittivity profiles using eight, twelve and sixteen mirror shapes, with FIG. 18A illustrating $\epsilon'$ along X=0 m, FIG. 18B illustrating $-\epsilon''$ along X=0 m, FIG. 18C illustrating $\epsilon'$ along Y=0.304 m, and FIG. 17D illustrating $-\epsilon''$ along Y=0.304 m.
Figure 18B:
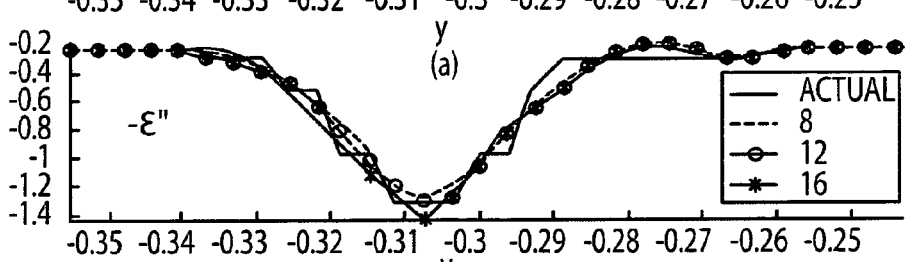
Figure 18C:
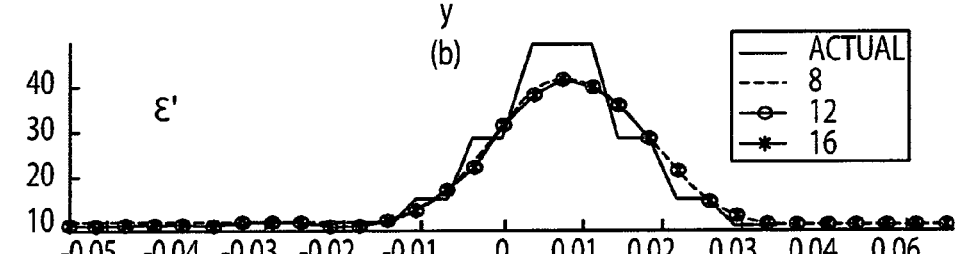
Figure 18D:
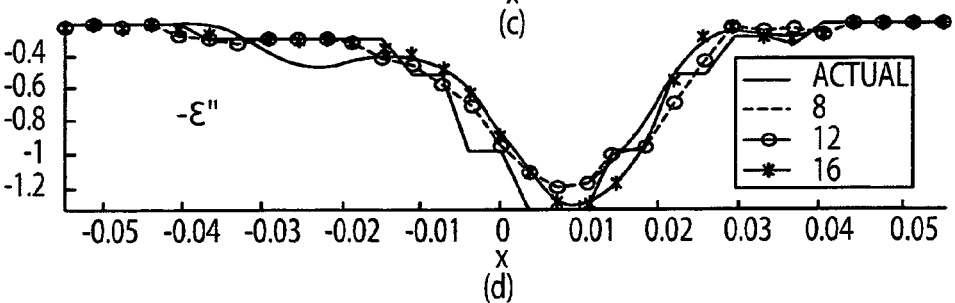

Two dimensional simulations for a lossy inhomogeneous cylindrical dielectric scatterer with 9 cm diameter were carried out for 700 MHz continuous wave excitation. The field measurements acquired at 24 locations on a 12 cm diameter circle surrounding the scatterer acquired for 20 optimal mirror shapes were used for inversion. The dielectric object was discretized using a finite element mesh with 300 triangular elements and 600 nodes with a total 205 elements with unknown permittivity. FIG. 16 shows the two-dimensional mesh of the inhomogeneous dielectric scatterer with background permittivity $\epsilon 1$. The permittivity of the scatterer increases from $\epsilon 2$ in the periphery to $\epsilon 5$. The permittivity values used for tomographic reconstruction are listed in Table 2.

TABLE 2

| Medium | Permittivity ($\epsilon' - j\epsilon''$) (Farads/m) |
|---|---|
| $\epsilon 1$ | 9.5000 − 0.2300i |
| $\epsilon 2$ | 9.5000 − 0.3000i |
| $\epsilon 3$ | 15.1452 − 0.5229i |
| $\epsilon 4$ | 28.5263 − 0.9833i |
| $\epsilon 5$ | 49.6133 − 1.3233i |

Twenty optimal mirror shapes used in inversion were chosen as per the procedure explained above. An analysis of the minimal number of mirror shapes required for permittivity reconstruction was carried by using field measurements from eight, twelve and sixteen mirror shapes. The inversion algorithm was initialized with the background permittivity and the estimate at each iteration was constrained using generous upper and lower bounds. Identical scaling ($\alpha$) and regularization ($\lambda$) parameters were used for reconstruction using a different number of mirror shapes.

FIGS. 17A-17H compares the tomographic images reconstructed using eight, twelve and sixteen mirrors at the 68th iteration for the zeroth order regularization technique. FIGS. 18A-18D compare the permittivity profile along horizontal and vertical transects through the dielectric object at the same iteration. The filtering property of the regularization technique resulted in a smoothed reconstruction of the unknown permittivity. Tomographic reconstructions shown in FIGS. 17A-17H imply that the inversion result improves with increase in the number of mirror shapes though acceptable results can be obtained even with eight mirrors shapes.

Unlike conventional tomography systems, in the proposed system the ability to acquire more field measurements for stable inversion is not limited by the number of transceiver antennas. The reconstruction results demonstrate the feasibility of this novel microwave tomography system which employs a deformable mirror and yields a multitude of field measurements for permittivity reconstruction using a fixed transmitter antenna.

The permittivity reconstructions of the inhomogeneous dielectric scatterer obtained using different number of mirror shapes demonstrate the merit of the proposed imaging technique in yielding a multitude of field measurements without increasing the number of receiver antennas. The proposed system avoids issues with antenna switching and compensation algorithms for the neighboring non-active antennas and only requires a control circuit for applying the potential distribution to the deformable mirror assembly for multi-view field measurements.

Figure 19:
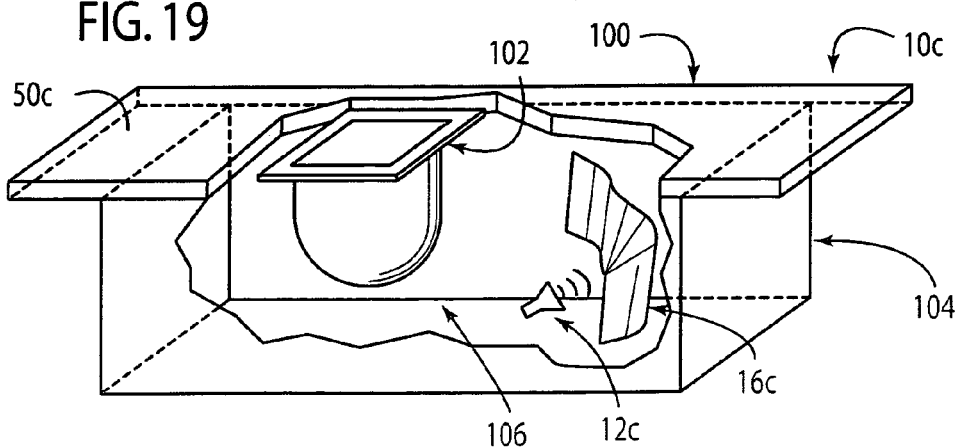
FIG. 19 illustrates a perspective view of a localized hyperthermia setup for breast cancer treatment using a deformable mirror.

FIG. 19 generally designates another embodiment of the present invention, having a fifth embodiment for the system. The system 10c of FIG. 19 is preferably used for treating breast cancer. In the United States, breast cancer is the second leading cause of cancer deaths amongst women and it is anticipated that one in every eight American women will succumb to breast cancer before the age of 90. In recent years, hyperthermia and ablation have been suggested as an alternate adjuvant therapy to radiation and chemotherapy treatment of breast cancer. Clinical prototypes developed for radio frequency hyperthermia often employ a phased array or multiple antenna arrangement to elevate the temperature at the tumor site for selective tissue heating. FIG. 19 illustrates an alternative mode of hyperthermia/ablation treatment using a deformable membrane mirror 16c. The deformable mirror 16c with a reflective coating functions as an adaptive focusing mirror and delivers preferential energy deposition at a tumor site in a breast. The proposed hyperthermia technique is devoid of the complexities associated with other radio frequency approaches such as the need for antenna amplitude/phase control for regional focusing.

FIG. 19 illustrates the proposed localized hyperthermia/ablation setup for breast cancer treatment using a deformable membrane mirror 16c. The imaging system comprises a fixed directional microwave source 12c and the deformable membrane mirror 16c with a reflective coating inside a treatment tank 104 of a tank and table 50c system containing a suitable coupling solution 106. The function of the deformable mirror 16c is to focus an incident electromagnetic field at the cancerous tissue positioned in a breast receptacle 102. With the knowledge of the spatial location of the tumor, the shape of the flexible mirror 16c is deformed to achieve preferential electromagnetic energy deposition at the tumor. The hyperthermia/ablation system 10c uses the deformable mirror 16c with an appropriate coating to reflect the incident electromagnetic field.

The efficacy of the proposed technique depends on determining the mirror shape that will yield a focal peak at the tumor site. Let $S_t(\bar{r})$ and $S_b(\bar{r})$ define the tumor volume and the breast volume excluding the tumor and $p_s(\bar{r})$, $p_t(\bar{r})$ be the locations of the microwave source and tumor center. For a given tumor and source location, the aim is to find a reflective surface $f(\bar{r})$ such that the ratio of the field in $S_t(\bar{r})$ and $S_b(\bar{r})$ is maximized. A search algorithm is implemented to find a set of contiguous points $p(\bar{r})$ in the region near the source such that the field incident on these contiguous points $p(\bar{r})$ yields a piecewise smooth shape $f(\bar{r})$. The search space is chosen such that the maximum dimension of the resultant surface is larger than $\lambda_c$ wavelength in the coupling solution. Such a reflective mirror shape can be achieved by applying the appropriate potential distribution to the underlying CMOS circuits of the deformable mirror assembly.

Numerical simulations in two dimensions were used to study the feasibility of dynamically changing the mirror shape for hyperthermia treatment. In two-dimensional simulations, the directional microwave source was approximated by a line source with a photoelectric backing to provide a directional field pattern. For a given $p_s(\bar{r})$ and $p_t(\bar{r})$, the mirror shape was decided using the ray tracing technique. The criteria that the maximum dimension of $f(\bar{r})$ be larger than $\lambda_c$ enables one to use ray tracing techniques to obtain an initial estimate of the mirror shape. The field pattern produced by the estimated mirror surface in the absence of the breast was calculated by solving the integral equation, $$\phi(\vec{\rho}) = J_z^{im} \otimes G_{2D} - \frac{\omega\mu_0}{4}\int_{\Gamma P} J_z^P(\vec{\rho}')G_{2D}(k_c|\vec{\rho}-\vec{\rho}'|)d\Gamma' - \frac{\omega\mu_0}{4}\int_{\Gamma M} J_z^m(\vec{\rho}')G_{2D}(k_1|\vec{\rho}-\vec{\rho}'|)d\Gamma'.$$

Figure 20A:
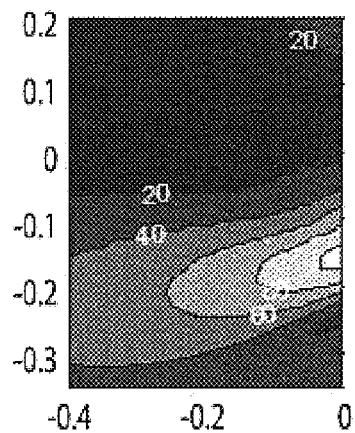
FIGS. 20A-20C illustrate field patterns inside a coupling medium at 700 MHz (FIG. 20A), 900 MHz (FIG. 20B) and 1000 MHz (FIG. 20C).
Figure 20B:
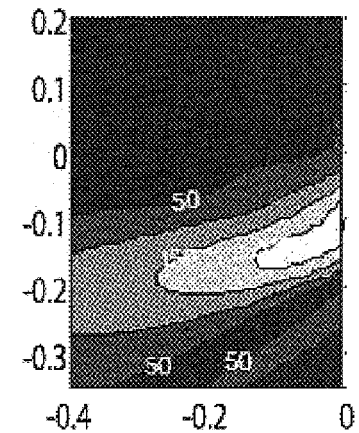
Figure 20C:
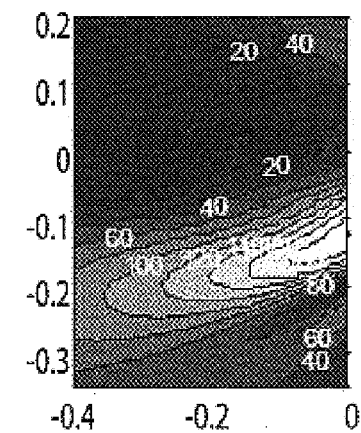

In the above equation, $J_z^{im}$ is the impressed line current density, $G_{2D}$ is the two-dimensional scalar Green's function and $J_z^P$, $J_z^M$ are the induced current densities on the line source's photoelectric backing and the deformable reflective mirror. The field pattern maintained by one such mirror shape for different operating frequencies is shown in FIGS. 20A-20C. The collimated field pattern in FIGS. 20A-20C demonstrates the potential of the deformable mirror in localized hyperthermia/ablation.

Figure 21A:
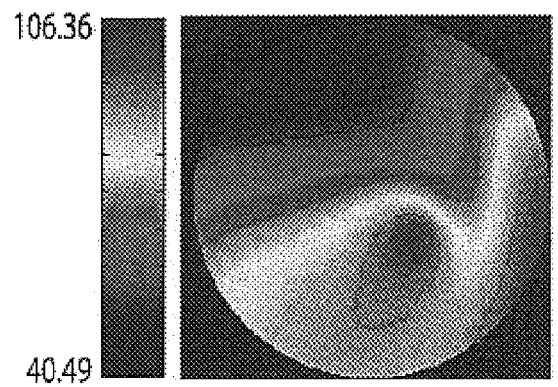
FIG. 21A illustrates a field pattern inside a breast model at 900 MHz.
Figure 21B:
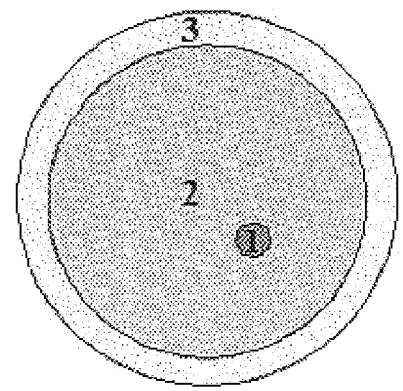
FIG. 21B is a two-dimension model of a breast with a tumor.

The field maintained by the deformable mirror inside the breast tissue was calculated to evaluate preferential energy deposition for hyperthermia/ablation treatment. The breast was modeled as an infinitely long regular dielectric cylinder of diameter 9 cm with the tumor located slightly off center as in FIG. 21B. The field pattern maintained by the deformable reflective mirror inside the breast tissue was computed by solving the finite element boundary integral (FEBI) equation with appropriate boundary conditions. The FEBI method emulates a fictitious radiation boundary using the boundary integral equation while employing the finite element method inside the breast. Instead of employing absorbing and perfectly matched layers as is commonly done, the boundary is imposed close to the breast resulting in very few unknowns. FIG. 21A shows the field pattern maintained by the deformable mirror inside the breast at 900 MHz for the permittivity values listed in Table 3. The high electrical contrast in the conductivity between the normal and malignant breast tissue results in a preferential heating of the tumor cells inside the breast.

TABLE 3

| Medium | $\epsilon'$ | $\epsilon''$ |
|---|---|---|
| 1 | 39.5 | −1.36 |
| 2 | 9.5 | −0.6 |
| 3 | 9.5 | −0.23 |

$\epsilon = \epsilon' + J\epsilon''$

The microwave hyperthermia/ablation treatment for breast cancer employs a deformable membrane mirror to focus the incident electromagnetic field towards the target tumor and achieves selective tumor heating sparing the surrounding tissue. With the help of a simple search algorithm, the potential distribution applied to the mirror actuator array can be adjusted in a feedback loop to focus the electromagnetic field to desired depths. The deformable mirror hyperthermia/ablation assembly with a single fixed microwave source supplements the functionality of the phased arrays and multiple antennas used in conventional radio frequency hyperthermia techniques.

It is to be understood that variations and modifications can be made on the aforementioned structure without departing from the concepts of the present invention. For example, the container scanning system 10a described above can be used to can containers, vehicles and people at ports, border crossings, jails, military bases and other sensitive installations by having the containers, vehicles and people slowly move between the deformable mirror 16a and the detector array 18a to determine if the containers, vehicles and/or people are carrying dangerous material. Moreover, it is contemplated that more than one deformable mirror (e.g., three) could be used in any of the systems described above. Furthermore, it is to be understood that such concepts are intended to be covered by the following claims unless these claims by their language expressly state otherwise.

We claim:

1. A method of providing cancer therapy to an object comprising:
    emitting rays with a source array;
    reflecting the rays emitted by the source array off of a deformable mirror and into the object; and
    destroying cancerous cells in the object with energy from the rays;
    wherein the rays are ultrasonic waves and heat from absorption of the ultrasonic waves destroys the cells.

2. A method of providing cancer therapy to an object comprising:
    emitting rays with a source array;
    reflecting the rays emitted by the source array off of a deformable mirror and into the object; and
    destroying cancerous cells in the object with energy from the rays;
    wherein the rays are microwaves and heat from absorption of the microwaves destroys the cells.

* * * * *

UNITED STATES PATENT AND TRADEMARK OFFICE
CERTIFICATE OF CORRECTION

PATENT NO.        : 7,425,193 B2
APPLICATION NO.   : 11/438639
DATED             : September 16, 2008
INVENTOR(S)       : Satish S. Udpa et al.

It is certified that error appears in the above-identified patent and that said Letters Patent is hereby corrected as shown below:

Col. 4, line 21, "--68th" should be -- 68th --.

Col. 15, line 1, "p[with a line above it] $\phi(\bar{p})$" should be -- p[with an arrow pointing right above it] $\phi(\vec{p})$ -- (two occurrences).

Col. 15, line 12, "p[with a line above it] $\phi(\bar{p}) = 0; \bar{p} \in \Gamma^M, \Gamma^P$" should be -- p[with an arrow pointing right above it] $\phi(\vec{p}) = 0; \vec{p} \in \Gamma^M, \Gamma^P$ -- (two occurrences).

Col. 15, line 46, "f(u)" should be -- f[super u] $f(u)$ --.

Col. 15, line 47, "f[sub p](u)" should be -- f[sub p][super (u)] $f_p(u)$ --.

Col. 15, line 48, "1[greater than symbol with two underscores] p [greater than symbol with two underscores] P $1 \leqq p \leqq P$" should be -- 1[greater than symbol with one underscore] p [greater than symbol with one underscore] P $1 \leq p \leq P$ --.

Col. 16, line 11, "p[with a line above it] $\phi^m(\bar{p})$" should be -- p[with an arrow pointing right above it] $\phi^m(\vec{p})$ --.

Col. 18, lines 9, 10, 11, 13, and 15, "(r[with a line above it]) $S_t(\bar{r})$" should be -- (r[with an arrow pointing right above it]) $S_t(\vec{r})$ --.

Col. 18, line 17, 28, and 30, "(r[with a line above it]) $f(\bar{r})$" should be -- (r[with an arrow pointing right above it]) $f(\vec{r})$ --.

UNITED STATES PATENT AND TRADEMARK OFFICE
CERTIFICATE OF CORRECTION

PATENT NO. : 7,425,193 B2
APPLICATION NO. : 11/438639
DATED : September 16, 2008
INVENTOR(S) : Satish S. Udpa et al.

It is certified that error appears in the above-identified patent and that said Letters Patent is hereby corrected as shown below:

Col. 18, line 40, "($k_1$]

$$\phi(\vec{\rho}) = J_z^{im} \otimes G_{2D} - \frac{\omega\mu_0}{4}\int_{\Gamma^P} J_z^P(\vec{\rho}')G_{2D}(k_1|\vec{\rho}-\vec{\rho}'|)d\Gamma' - \frac{\omega\mu_0}{4}\int_{\Gamma^M} J_z^M(\vec{\rho}')G_{2D}(k_c|\vec{\rho}-\vec{\rho}'|)d\Gamma'$$

" should be

-- $k_c$] $\phi(\vec{\rho}) = J_z^{im} \otimes G_{2D} - \frac{\omega\mu_0}{4}\int_{\Gamma^P} J_z^P(\vec{\rho}')G_{2D}(k_c|\vec{\rho}-\vec{\rho}'|)d\Gamma' - \frac{\omega\mu_0}{4}\int_{\Gamma^M} J_z^M(\vec{\rho}')G_{2D}(k_c|\vec{\rho}-\vec{\rho}'|)d\Gamma'$ --.

Signed and Sealed this

Twenty-seventh Day of January, 2009

JOHN DOLL
*Acting Director of the United States Patent and Trademark Office*